US012599562B2

(12) United States Patent
Garcia-Contreras et al.

(10) Patent No.: US 12,599,562 B2
(45) **Date of Patent: *Apr. 14, 2026**

(54) NANOCRYSTAL MICROPARTICLES OF POORLY SOLUBLE DRUGS AND METHODS OF PRODUCTION AND USE THEREOF

(71) Applicant: The Board of Regents of the University of Oklahoma, Norman, OK (US)

(72) Inventors: Lucila Garcia-Contreras, Edmond, OK (US); Sevim Manolya Hatipoglu, Oklahoma City, OK (US); Doris Mangiaracina Benbrook, Oklahoma City, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 342 days.

This patent is subject to a terminal disclaimer.

(21) Appl. No.: 18/145,334

(22) Filed: Dec. 22, 2022

(65) Prior Publication Data

US 2023/0139842 A1 May 4, 2023

Related U.S. Application Data

(63) Continuation-in-part of application No. 17/171,151, filed on Feb. 9, 2021, now Pat. No. 11,534,397, which is a continuation-in-part of application No. 16/183,368, filed on Nov. 7, 2018, now abandoned.

(60) Provisional application No. 62/583,755, filed on Nov. 9, 2017.

(51) Int. Cl.
*A61K 9/16* (2006.01)
*A61K 31/382* (2006.01)

(52) U.S. Cl.
CPC .......... *A61K 9/1682* (2013.01); *A61K 9/1623* (2013.01); *A61K 9/1635* (2013.01); *A61K 31/382* (2013.01)

(58) Field of Classification Search
CPC .. A61K 9/1682; A61K 9/1623; A61K 9/1635; A61K 31/382
See application file for complete search history.

(56) References Cited

U.S. PATENT DOCUMENTS

| | | | | |
|---|---|---|---|---|
| 5,091,188 A * | 2/1992 | Haynes | A61K 9/127 | 424/408 |
| 6,586,460 B1 | 7/2003 | Berlin et al. | | |
| 7,612,107 B2 | 11/2009 | Benbrook et al. | | |
| 2002/0102294 A1* | 8/2002 | Bosch | A61K 9/1694 | 424/490 |

(Continued)

OTHER PUBLICATIONS

American Cancer Society, Cancer Facts & Figures 2016; Atlanta, GA.; American Cancer Society (2016), pp. 1-66.

(Continued)

*Primary Examiner* — Jianfeng Song
(74) *Attorney, Agent, or Firm* — Dunlap Codding, P.C.

(57) ABSTRACT

Microparticulate drug compositions comprising nanocrystals of poorly soluble drugs combined with a carrier are disclosed. Also disclosed are pharmaceutical compositions that include the microparticulate drug compositions. Further disclosed are methods of preparing and using the microparticulate drug compositions/pharmaceutical compositions.

17 Claims, 9 Drawing Sheets

(56) References Cited

U.S. PATENT DOCUMENTS

2004/0156859 A1* 8/2004 Ezrin .................... A61P 11/08 514/397
2010/0260858 A1 10/2010 Ruddy et al.
2013/0184323 A1* 7/2013 Benbrook ............. A61K 31/38 514/432

OTHER PUBLICATIONS

Benbrook, et al.; "Chemoprevention of Colon and Small Intestinal Tumorigenesis in APC(min/+) Mice by SHetA2 (NSC721689) Without Toxicity," Cancer Prev Res (2013); 6(9):908-916.
Chen, et al.; "Nanonization Strategies for Poorly Water-Soluble Drugs," Drug Discovery Today; (2011); 16(7/8):354-360.
Garcia-Contreras, et al.; "Dry Powder PA-824 Aerosols for Treatment of Tuberculosis in Guinea Pigs," Antimicrobial Agents and Chemotherapy (2010); 54(4):1436-1442.
Garcia-Contreras, et al.; "Pharmacokinetics of Aerosolized Rifampicin Large Porous Particles in the Guinea Pig," Respiratory Drug Delivery (2006); Healthcare International Publishing, LCC: David River Grove, IL.; pp. 873-876.
Hatipoglu, et al.; "Inhalable Microparticulate SHetA2 Nanocrystals for Lung Cancer Treatment," University of Oklahoma Health Sciences Center Graduate Research Education and Technology (GREAT) Symposium, Oklahoma City, OK. USA, Mar. 2017.
Hatipoglu, et al.; "SHetA2 Nanocrystals as Novel Therapy to Treat Lung Cancer: Formulation and Characterization," AAPS Annual Meeting and Exposition, Denver, CO.; Nov. 13-17, 2016.
Hatipoglu, et al.; "Pharmacokinetics of Inhalable Microparticulate SHetA2 Nanocrystals for Lung Cancer Treatment," AAPS Annual Meeting and Exposition, Nov. 12-15, 2017.
Heyder, et al.; "Deposition of Particles in the Human Respiratory Tract in the Size Range 0.005-15 μm," J. Aerosol Sci., (1986); 17(5): 811-825.
Heyder, et al.; "Mathematical Models of Particle Deposition in the Human Respiratory Tract*," J. Aerosol Sci., (1984); 15(6):697-707.
Ibrahim, et al.; "Optimization of Inhalable ShetA2 Microparticles for Tuberculosis Treatment," AAPS conference, Orlando, FL., Oct. 25-29, 2015.
Ibrahim, et al.; "Dissolution Studies for Inhalable SHetA2 Dry Powder Using Modified Flow through Cell Dissolution Apparatus," AAPS Annual Meeting and Exposition, Denver CO., Nov. 13-17, 2016.
Ige, et al.; "Fabrication of Fenofibrate Nanocrystals by Probe Sonication Method for Enhancement of Dissolution Rate and Oral Bioavailability," Colloids and Surfaces B: Blointerfaces (2013), 108:366-373.
Jinno, et al.; "Effect of Particle Size Reduction on Dissolution and Oral Absorption of a Poorly Water-Soluble Drug, Cilostazol, in Beagle Dogs," Journal of Controlled Release, (2006), 111:56-64.
Kabirov, et al.; "Oral Toxicity and Pharmacokinetic Studies of SHetA2, a New Chemopreventive Agent, in Rats and Dogs," Drug and Chemical Toxicology (2013), 36(3):284-295.
Keck, et al.; "Second Generation of Drug Nanocrystals for Delivery of Poorly Soluble Drugs: SmartCrystals Technology," Dosis (2008) 24:124-128.
Lin, et al.; "CAAT/Enhancer Binding Protein Homologous Protein-Dependent Death Receptor 5 Induction is a Major Component of SHetA2-Induced Apoptosis in Lung Cancer Cells," Cancer Res. (2008), 68(13):5335-5344.
Lipinski, et al.; "Experimental and Computational Approaches to Estimate Solubility and Permeability in Drug Discovery and Development Settings," Advanced Drug Delivery Reviews (2001), 46:3-26.
Naylor, et al.; "Anti-Cancer Activities and Interaction of Imiquimod and Flex-Het, SHetA2, in Melanoma and Ovarian Cancer," Journal of Cancer Therapy (2013), 4:7-19.
Sawant, et al.; "Drug Nanocrystals: Novel Technique for Delivery of Poorly Soluble Drugs," International Journal of Science Innovations and Discoveries (2011), 1(3):1-15.
Sinha, et al.; "Bottom-up Approaches for Preparing Drug Nanocrystals: Formulations and Factors Affecting Particle Size," International Journal of Pharmaceutics (2013), 453:126-141.
Wood, et al.; "Aerosolised Antibacterials for the Prevention and Treatment of Hospital-Acquired Pneumonia," Drugs (2007), 67(6):903-914.
Yan Chan, et al.; "A Novel Dry Powder Inhalable Formulation Incorporating Three First-Line Anti-Tubercular Antibiotics," European Journal of Pharmaceutics and Biopharmaceutics (2013), 83:285-292.
Ibrahim, et al; A Novel Tuberculosis Treatment: Inhalable SHetA2 Microparticles for Immediate Release and Macrophage Targeting, Respiratory Drug Delivery (2016) Annual Meeting and Exposition, Scottsdale AZ. , April 17-21, 2016, pp. 591-594.
U.S. Appl. No. 16/183,368, filed Nov. 7, 2018; Office Action dated Feb. 7, 2020.
U.S. Appl. No. 16/183,368, filed Nov. 7, 2018; Amendment and Response to Office Action dated Aug. 7, 2020.
U.S. Appl. No. 16/183,368, filed Nov. 7, 2018; Final Office Action dated Sep. 24, 2020.
U.S. Appl. No. 17/171,151, filed Feb. 9, 2021; Office Action dated Jan. 7, 2022.
U.S. Appl. No. 17/171,151, filed Feb. 9, 2021; Amendment and Response to Office Action dated Jul. 7, 2022.
U.S. Appl. No. 17/171,151, filed Feb. 9, 2021; Notice of Allowance dated Aug. 18, 2022.
Benbrook, et al.; "Biologically Active Heteroarotinoids Exhibiting Anticancer Activity and Decreased Toxicity," Journal of Medicinal Chemistry, (1997), 40(22):3567-3583.
Brown, et al.; "Novel Heteroarotinoids as Potential Antagonists of Mycobacterium bovis BCG," J. Med. Chem. (2004), 47(4):1008-1017.
Dhar, et al.; "Synthesis, Structure-Activity Relationships, and $RAR^{\gamma}$-Ligand Interactions of Nitrogen Heteroarotinoids," J. Med. Chem. (1999), 42(18):3602-3614.
Gnanasekeran et al.; "Synthesis and Evaluation of Second Generation Flex-Het Scaffolds Against the Human Ovarian Cancer A2780 Cell Line," European Journal of Medicinal Chemistry (2015), 96:209-217.
Le, et al.; "Heteroarotinoids with Anti-Cancer Activity Against Ovarian Cancer Cells," The Open Medicinal Chemistry Journal (2007), 1:11-23.
Liu, et al.; "Synthesis of Flexible Sulfur-Containing Heteroarotinoids that Induce Apoptosis and Reactive Oxygen Species with Discrimination Between Malignant and Benign Cells," J. Med. Chem. (2004), 47(4):999-1007.
Liu, et al.; "Development of Flexible-Heteroarotinoids for Kidney Cancer," Mol Cancer Ther (May 2009), 8(5):1227-1238.
Zacheis, et al.; "Heteroarotinoids Inhibit Head and Neck Cancer Cell Lines in Vitro and In Vivo Through Both RAR and RXR Retinoic Acid Receptors," J. Med. Chem. (1999), 42(21):4434-4445.

* cited by examiner

NANOCRYSTAL MICROPARTICLES OF POORLY SOLUBLE DRUGS AND METHODS OF PRODUCTION AND USE THEREOF

CROSS REFERENCE TO RELATED APPLICATIONS/INCORPORATION BY REFERENCE STATEMENT

This application is a continuation-in-part of U.S. patent application Ser. No. 17/171,151, filed Feb. 9, 2021, now issued U.S. Pat. No. 11,534,397, issued Dec. 27, 2022; which is a continuation-in-part of U.S. patent application Ser. No. 16/183,368, filed Nov. 7, 2018, now abandoned; which claims benefit under 35 USC § 119(e) of U.S. Provisional Application No. 62/583,755, filed Nov. 9, 2017. The entire contents of the above-referenced patent applications are hereby expressly incorporated herein by reference.

BACKGROUND

One of the main challenges in the treatment of lung diseases such as tuberculosis, cancer, and fungal infections is the poor water solubility of some of the most effective therapeutic compounds to treat these diseases, which causes low oral bioavailability of these therapeutic compounds. As a result, higher doses of these compounds must be used to treat these conditions effectively. However, these high doses can also cause significant adverse effects that decrease the quality of life of patients.

For example, lung cancer is the leading cause of cancer death worldwide and accounts for 26-30% of all cancer deaths in the United States. The two major types of lung cancer are small cell lung cancer (SCLC) and non-small cell lung cancer (NSCLC); NSCLC accounts for 85-90% of lung cancers. From NSCLC, the adenocarcinoma is usually found in the bronchio-alveolar region of the lung. Surgery is the standard of care for stage I NSCLC, whereas for stage II and IIIA adjuvant, cisplatin-based chemotherapy remains the gold standard for completely resected NSCLC tumors. Chemotherapy is usually given systemically (oral or IV), with just a small fraction of the drug reaching the lung, while most is distributed elsewhere in the body. As a result, treatment usually involves administration of high doses, which results in severe side effects and decreased quality of life for the patient.

Cancer chemotherapy is limited by the often poor solubility of drugs and by the toxicity caused by drugs, including (but not limited to) cytotoxic agents which are the most widely used anticancer therapies. To overcome the handicaps of cytotoxic agents, new molecular targeting therapies have been developed. Although they have an improved toxicity profile, administrations of these agents continuously over long time periods causes chronic toxicity, which still remains a key limiting factor.

The number of poorly soluble drugs in use has dramatically increased over the last ten years. Poor solubility in water is associated with low bioavailability. If the drug is not soluble, its absorption will be greatly reduced, and it will not reach the site of action. Efforts have been made to increase the solubility of these poorly soluble compounds. However, the methods which are used to increase the solubility of these poorly soluble drugs are limited due to their chemistry. Some methods include chemical modification or formulation of the compound in a pharmaceutical dosage form. However, chemical modification decreases the effectiveness of some compounds, and traditional dosage forms require the use of excipients that usually increase the amount of material that the patient ingests and may not decrease the required dose.

A common approach to increase the dissolution rate of therapeutic compounds is the reduction of their particle size to micron sizes by milling. Increasing surface area by reducing the size of particles provides a high surface to volume ratio, which effectively increases the dissolution rate by increasing saturation solubility. Yet this size reduction is often not sufficient to increase solubility and drug absorption to therapeutic levels.

As noted, direct pulmonary delivery of poorly soluble compounds in powder formulations can increase their therapeutic efficacy for lung diseases, but this approach is limited by the amount of powder that can be dosed at one time by this route. This approach is further limited when these dry powder formulations contain large amounts of excipients that increase the size of the inhaled dose and that are likely to cause side effects in the respiratory tract and in the lungs. This is the main limitation for the pulmonary delivery of therapeutic agents formulated in nanoparticles, including (but not limited to) polymeric nanoparticles and liposomes. Moreover, pulmonary delivery of nanocrystals by themselves would be difficult, since due to their small size they would simply be exhaled, owing to their low inertia.

It has been hypothesized that nanocrystals (NCs) having sizes below the micron range and consisting of 100% drug may be capable of achieving therapeutic concentration at the site of drug action for these lung diseases with very small powder doses. Nevertheless, dry powder NCs are subject to problems of aggregation due to strong electrostatic forces exhibited by particles of that size, which result in the generation of highly poly-dispersed aerosols consisting of irregular sized particles. Three basic techniques are conventionally used to generate nanocrystals, including milling, precipitation, and homogenization methods.

Elan Nanosystems (San Francisco, CA) produces NC products using a proprietary NANOCRYSTAL® technology based on a pearl mill technology. The resulting NC material is used mostly in oral suspensions and tablets. RAPAMUNE® (rapamycin; Pfizer Inc., New York City, NY), for example, is used to avoid organ rejection after a kidney transplantation; it is available in two formulations such as oral suspension and tablet. EMEND® (aprepitant; Merck & Co., Inc., Kenilworth, NJ) is used to treat emesis; the formulation is prepared by nanonization, and the drug nanocrystals are packed in hard gelatin capsule as pellets.

TRICOR® (fenofibrate) is a drug developed and marketed by Abbott Laboratories (Chicago, IL). It is used in tablet form for treatment as adjunctive therapy for hypercholesterolemia or mixed dyslipidemia. MEGACE ES® (megestrol acetate; Par Pharmaceutical Companies, Inc., Spring Valley, NY), is a synthetic progestin known as megestrol which is used to help patients who are suffering from chemotheraphy and HIV infection to gain weight. It is formulated as a nanocrystal suspension and administered orally.

DETAILED DESCRIPTION

Figure 1:
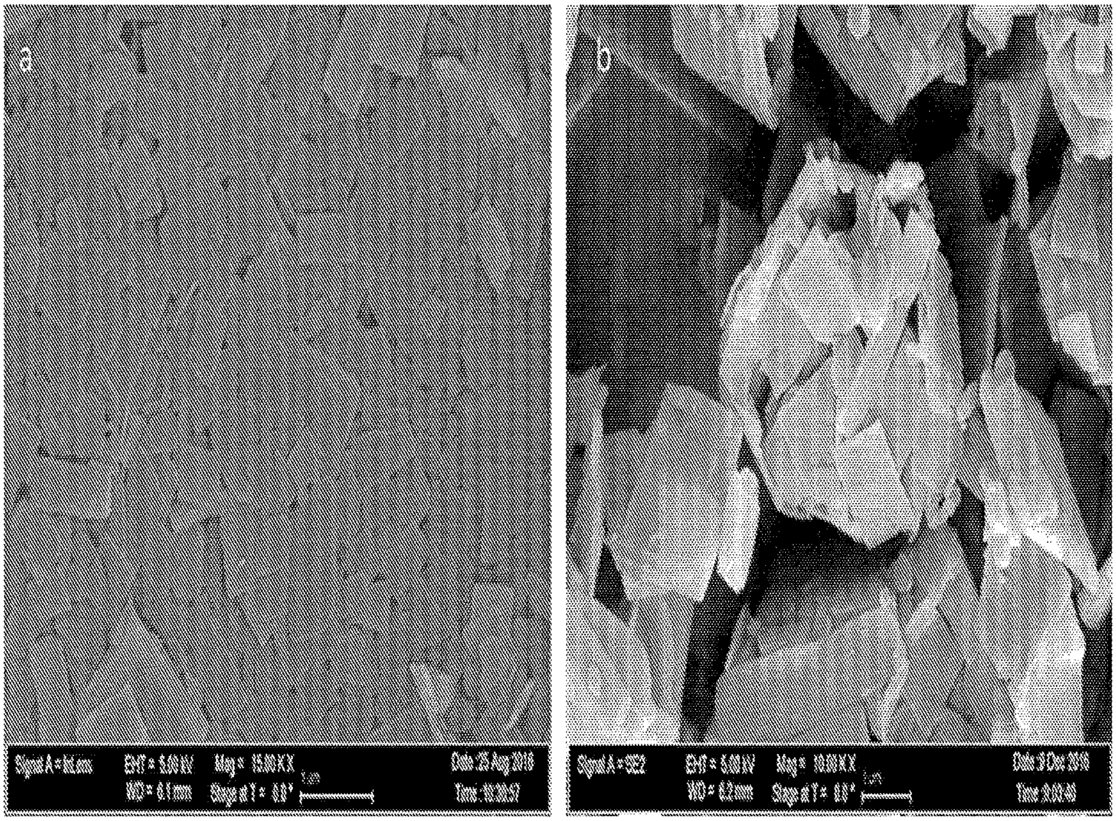
FIG. 1 shows SEM images of (a) SHetA2 nanocrystals (NCs) and (b) microparticles (MPs) produced from the SHetA2 NCs.

The present disclosure, in at least certain non-limiting embodiments, is directed to the formation of drug microparticles by spray drying suspensions of drug nanocrystals suspended in a solvent, thereby reducing polydispersity and enabling customization of the size distribution and average size and volume of the microparticles. In certain non-limiting embodiments, the microparticles have an average size which enables the targeting of specific lung regions (e.g., alveoli) for improved therapy when the microparticles are administered, particularly as dry powder aerosols. Direct pulmonary administration of drugs formulated by the approach disclosed herein results in achieving drug concentrations in the lung that other routes of administration, such as oral or parenteral routes, frequently cannot attain. In other non-limiting embodiments, the microparticles are formed to have an average particle size which enables the microparticles to flow more easily during dosage manufacturing processes, thus facilitating the making of drug capsules and tablets. In other non-limiting embodiments, the microparticles can be formulated into creams, ointments, or implants.

Before further describing various embodiments of the compounds, compositions, and methods of the present disclosure in more detail by way of exemplary description, examples, and results, it is to be understood that the compounds, compositions, and methods of the present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning, and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure. Thus, while the compounds, compositions, and methods of the present disclosure have been described in terms of particular embodiments, it will be apparent to those of skill in the art that variations may be applied to the compounds, compositions, and/or methods and in the steps or in the sequence of steps of the methods described herein without departing from the concept, spirit, and scope of the inventive concepts described herein.

All patents, patent applications, and non-patent publications mentioned in the specification or referenced in any portion of this application are herein expressly incorporated by reference in their entirety to the same extent as if each individual patent, application, or publication was specifically and individually indicated to be incorporated by reference. Non-limiting examples thereof include U.S. Pat. Nos. 6,586,460; 7,612,107; 9,511,026; 9,750,696; and 9,795,562; U.S. patent application Ser. Nos. 17/171,151 and 16/183,368, and U.S. Provisional Patent Application No. 62/583,755.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As noted above, any numerical range listed or described herein is intended to include, implicitly or explicitly, any number or sub-range within the range, particularly all integers, including the end points, and is to be considered as having been so stated. For example, "a range from 1.0 to 10.0" is to be read as indicating each possible number, including integers and fractions, along the continuum between and including 1.0 and 10.0, that is, having a minimum value equal to or greater than 1.0 and a maximum value equal to or less than 10.0, such as, for example, 3.25 to 8.65. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. Thus, even if a particular data point within the range is not explicitly identified or specifically referred to, it is to be understood that any data points within the range are to be considered to have been specified, and that the inventor(s) possessed knowledge of the entire range and the points within the range.

As used in this specification and claims, the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, observer error, wear and tear, and combinations thereof, for example. The terms "about" or "approximately," where used herein when referring to a measurable value such as an amount, a temporal duration, and the like, are meant to encompass, for example, variations of ±20%, or ±15%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, or at least 80% of the time, or at least 90% of the time, or at least 95% of the time, or at least 98% of the time.

As used herein, any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. In addition, the use of the terms "one embodiment" and "an embodiment" are not to be construed as limiting in any matter of the scope of the present disclosure.

The term "active agent" where used herein is intended to refer to a substance which possesses a biological activity relevant to the present disclosure, and particularly refers to therapeutic and diagnostic substances which may be used in methods described in the present disclosure. By "biologically active" is meant the ability to modify the physiological system of a cell, tissue, or organism without reference to how the active agent has its physiological effects. Where used herein, unless otherwise noted, the term "active agent" includes pharmaceutically-acceptable salts, hydrates, solvates, and amorphous solids thereof.

The term "pharmaceutically acceptable" refers to compounds and compositions which are suitable for administration to humans and/or animals without undue adverse side effects such as toxicity, irritation, and/or allergic response commensurate with a reasonable benefit/risk ratio. The compounds of the present disclosure may be combined with one or more pharmaceutically-acceptable excipients, including carriers, vehicles, diluents, and adjuvants which may improve solubility, deliverability, dispersion, stability, and/or conformational integrity of the compounds or conjugates thereof.

"Pharmaceutically acceptable salts" means salts of active agent compounds disclosed herein which are pharmaceutically acceptable, as defined above, and which possess the desired pharmacological activity. Such salts include (but are not limited to) acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include (but are not limited to) base addition salts which may be formed when acidic protons present are capable of reacting with inorganic or organic bases. Acceptable inorganic bases include (but are not limited to) sodium hydroxide, sodium carbonate, potassium hydroxide, aluminum hydroxide and calcium hydroxide. Acceptable organic bases include (but are not limited to) ethanolamine, diethanolamine, triethanolamine, tromethamine, N-methylglucamine and the like. It should be recognized that the particular anion or cation forming a part of any salt of the present disclosure is not critical, so long as the salt, as a whole, is pharmacologically acceptable. Additional non-limiting examples of pharmaceutically acceptable salts and their methods of preparation and use are shown in *Handbook of Pharmaceutical Salts: Properties, and Use* (P. H. Stahl & C. G. Wermuth eds., Verlag Helvetica Chimica Acta, 2002).

As used herein, the term "pure" or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer an organism to which the compositions of the present disclosure are applied and used, such as (but not limited to) a vertebrate or more particularly to a warm blooded animal, such as (but not limited to) a mammal or bird. Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention. Non-limiting examples of modes of administration include inhalation, oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the present disclosure may be designed to provide delayed, controlled, extended, and/or sustained release using formulation techniques which are well known in the art.

The terms "therapeutic composition" and "pharmaceutical composition" refer to a composition comprising a poorly soluble drug that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active ingredient, such as a poorly soluble drug, which is sufficient to exhibit a detectable therapeutic or treatment effect in a subject without excessive adverse side effects (such as substantial toxicity, irritation, and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit, or control in the occurrence, frequency, severity, progression, or duration of the condition, or an improvement in a symptom or an underlying cause or a consequence of the condition, or a reversal of the condition. A successful treatment outcome can lead to a "therapeutic effect" or "benefit" of ameliorating, decreasing, reducing, inhibiting, suppressing, limiting, controlling, or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most, or all adverse symptoms, complications, consequences, or underlying causes associated with the condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition (e.g., stabilizing), over a short or long duration of time (e.g., seconds, minutes, hours).

The active agents of the present disclosure can be combined into formulations or treatments that are synergistic. As used herein the terms "synergism," "synergistic," or "synergistic effect" refers to a therapeutic effect or result that is greater than the additive effects of each active agent used individually. Presence or absence of a synergistic effect for a particular combination of treatment substances can be quantified by using the Combination Index (CI) (e.g., Chou, Pharmacol Rev, 2006. 58(3): 621-81), wherein CI values lower than 1 indicate synergy and values greater than 1 imply antagonism. Combinations of the inhibitors and antagonists of the present disclosure can be tested in vitro for synergistic cell growth inhibition using standard cell lines for particular cancers, or in vivo using standard animal cancer models. A synergistic effect of a combination described herein can permit, in some non-limiting embodiments, the use of lower dosages of one or more of the components of the combination. A synergistic effect can also permit, in some non-limiting embodiments, less frequent administration of at least one of the administered active agents. Such lower dosages and reduced frequency of administration can reduce the toxicity associated with the administration of at least one of the therapies to a subject without reducing the efficacy of the treatment.

The term "coadministration" refers to administration of two or more active agents, e.g., a cardiac-targeted composition as described herein and another active agent. The timing of coadministration depends in part on the combination and compositions administered and can include administration at the same time, just prior to, or just after the administration of one or more additional therapies. "Coadministration" is meant to include simultaneous or sequential administration of the compound and/or composition individually or in combination. Thus, the preparations can also be combined, when desired, with other active substances (e.g., to reduce metabolic degradation). For example, the compositions described herein can be used in combination with one another, or with other active agents known to be useful in treating MI, and co-occurring conditions thereof.

Where used herein, the term "soluble" refers to the ability of a substance to dissolve in a solvent, such as water. Where used herein, the term "poorly soluble drug" (a.k.a., "poorly water-soluble drug" and "low solubility drug") refers to a drug or bioactive agent which requires from 1000 to 10000 parts of solvent for 1 part of solute, and/or is a Class II (high permeability, low solubility) or Class IV (low permeability, low solubility) drug according to the Biopharmaceutics Classification System (BCS). Non-limiting examples of such poorly soluble drugs which may be used in the microparticulate compositions as disclosed or otherwise contemplated herein include, but are not limited to, those listed in U.S. Pat. Nos. 9,795,562; 9,750,696; and 9,511,026.

Where used herein in reference to a poorly soluble drug, the term "unprocessed" (e.g., "unprocessed drug") refers to a feedstock form of the poorly soluble drug which is initially provided before being processed into nanocrystals or nanocrystal microparticles as described in the present disclosure.

Where used herein in reference to a poorly soluble drug, the term "amorphous" (e.g., "amorphous drug") refers to a form of the poorly soluble drug which has a disordered arrangement of molecules and which does not possess a distinguishable crystal lattice, for example (but not by way of limitation), a drug which has been spray-dried according to methods of the present disclosure, without having first been converted into nanocrystals according to methods of the present disclosure.

Where used herein in reference to a compound, the term "apparent solubility" refers to the concentration (g/L) of the compound in a solvent at apparent equilibrium (i.e., supersaturation).

Where used herein, the terms "sonication" or "sonicating" refer to using sound energy to agitate or deagglomerate nanoparticles in a suspension, generally at rates/frequencies <20 kHz (such as but not limited to 1 Hz-1000 Hz, 10 Hz-500 Hz, 10 Hz-100 Hz, 20 Hz-80 Hz, 25 Hz-75 Hz, 40 Hz-70 Hz, or 50 Hz-60 Hz).

Sonication (or probe sonication) is a process in which sound energy is directly administered to the media/sample by inserting a probe in it. Since the probe is in direct contact with the media/sample, the particles/solvent directly surrounding the probe large amounts of energy are hit directly with large amounts of energy causing the formation of bubbles that form and collapse in the surrounding solution, an event known as "cavitation." These systems require less power input and can deliver up to 20,000 W/L of energy into the processed medium. The properties of the sound energy (power and amplitude) can be controlled.

Where used herein, the terms "ultrasonication" or "ultrasonicating" refer to using rate/frequencies >20 kHz (e.g., in a range of 20 kHz-40 kHz), for homogenization of a fluid.

Ultrasonication (or bath sonication), is an indirect sonication method in which a water bath is used. Using this method, the ultrasonic energy is transmitted to a water bath and then into a vessel containing the media/sample. Since the bath sonicator separates/isolates samples from the energy source, it spreads the energy more diffusely throughout the bath and sample. Thus, higher power is required for the process, but the system only delivers 20-40 W/L of energy into the medium.

In the presently described methods, after the poorly soluble drug is dissolved in an organic solvent, the drug-organic solvent mixture is combined with an aqueous solvent (e.g., water), and a large amount of energy is required to create shear forces ("cavitation") and waves that disrupt the molecular interactions between the molecules of water and organic solvent. This large amount of energy is provided directly to the media with the probe sonication. The reduction in the molecular interactions limits the sizes of drug crystal nuclei and controls the rate of drug crystal formation. Subsequently, a smaller amount of energy is required to evaporate the organic solvent while maintaining constant the nanocrystal sizes. This smaller energy is provided by the bath sonicator (ultrasonication), since larger amounts of energy may break the drug nanocrystals being formed.

Organic solvents used in the methods of the present disclosure must be miscible in an aqueous solution (e.g., water). Examples of such organic solvents include, but are not limited to, acetone, acetonitrile, dimethylformamide, dimethyl sulfoxide, dioxane, methanol, ethanol, n-propanol, isopropanol, and tetrahydrofuran.

Where used herein, the term "controlled precipitation" refers to the process by which the sizes of the NCs are controlled during the nanocrystal formation process. Identifying the conditions for controlled precipitation of the nanocrystals includes, for example, (1) selecting a volume: volume ratio of the volume of the solvent in which the drug is dissolved, and the volume of aqueous solvent (e.g., water) with which the dissolved drug is combined; (2) selecting an energy level applied to this liquid mixture (sonication/ultrasonication power and amplitude), which controls the size and rate of crystal nuclei formation; and (3) selecting the time and energy that is applied to the mixture to evaporate the solvent and complete the full formation of nanocrystals.

In certain embodiments, the parameters of the methods of synthesis of the present disclosure can be determined by "Quality by Design" (QbD). QbD is a systematic approach to development that begins with predefined objectives and emphasizes identification of product performance and process understanding and process control, based on sound science and quality risk management. QbD approach has five main steps. Critical quality attributes (CQAs) are determined. This includes the steps of (1) design formulation and process to meet the product CQAs, (2) Understanding the impact of material and process parameters on product critical quality, (3) Identification of sources of variability in the API, excipients, or the employed formulation process; and (5) continuous monitoring of the process to ensure consistent quality.

The implementation of QbD in product development provides sufficient material and process knowledge that guides the manufacturing strategy and reduces the risks of failures and resolves any out of the specification result that may occur during quality control (QC) testing. Thus, proper application of QbD in the pharmaceutical industry speeds up the product development reduces cost and accelerate the product approval by the FDA.

For example, when it is desired to make a vaginal suppository of SHetA2, only the first 3 steps are need to attain the desired characteristics of the nanocrystals. In one embodiment, the desired characteristics for an SHetA2 vaginal suppository formulation are: i) ease of insertion; ii) fast drug release of from the base; and, iii) meet quality control specifications outlined by the United States Pharmacopoeia (USP). Thus, the critical quality attributes (CQA) in the optimum formulation were defined as (i) to be solid at room temperature and maintain physical integrity during administration; (ii) to disintegrate or melt within 5-10 minutes; and (iii) have content uniformity (85%-115%) and weight variation within 7.8%. The suppositories can be manufactured using a fusion molding method and USP stainless steel suppository molds. The formulation ingredients comprised a hydrophilic base (PEG mixture) or a lipophilic base (cocoa butter), drug and Kolliphor. These ingredients were entered at different proportions into the Design of Experiments (DoE) software (Design-Expert, version 8.0.1, Stat-ease®) to evaluate statistically the effects of the formulation components on the characteristics of the product (e.g., see (see Mahjabeen, S., Chandra, V., Hatipoglu, S. M., Benbrook, D. M. and Garcia-Contreras, L. "Optimization of a Vaginal Suppository Formulation to Deliver SHetA2 as a Novel Treatment for Cervical Dysplasia". *Journal of Pharmaceutical Sciences*. 2018; 107(2): 638-646). The QbD steps can also be used for implants or tablets, but the CQAs and method of manufacture as well as the excipients will be different.

Where used herein, the term "carrier ratio" refers to the percentage of total solids in a suspension that are highly soluble sugar(s) as compared to the percentage that are NCs. That is, an "X %" carrier ratio indicates that X % of the total solids are the carrier and (100−X) % of the total solids are NCs. For example, a 55% carrier ratio indicates that 55% of the total solids are the carrier and 45% of the total solids are NCs.

Where used herein, the term "highly soluble sugar" includes saccharides, particularly monosaccharides and disaccharides, including polyols, having a solubility of at least 50 g per 100 ml $H_2O$ at 20° C., and include, but are not limited to, sugar alcohols, alditols, glycols, polyols, saccharides, and polysaccharides. Highly soluble sugars used in the presently disclosed compositions may include, for example (but not by way of limitation), cyclitol, acarviocin, aminocyclitol, bornesitol, ciceritol, conduritol, decahydroxycyclopentane, 5-deoxyinositol, dodecahydroxycyclohexane, ononitol, pinitol, pinpollitol, quebrachitol, theogallin, 3,4,5-tri-O-galloylquinic acid, inositol, inositol pentakisphosphate, cis-inositol, D-chiro-inositol, L-chiro-inositol, epi-inositol, neo-inositol, muco-inositol, neo-inositol, scyllo-inositol, sorbitol, threitol, arabitol, galactitol, iditol, volemitol, sorbitol, fucitol, xylitol, lactitol, erythritol, lactitol, maltitol, phytic acid, quinic acid, propylene glycol, 1,2-propanediol, ethylene glycol, low molecular weight polyethylene glycols (e.g., C2-C10), vegetable glycerine, dipropylene glycol, erythulose, glycerol, panthenol, arabinose, bis-HPPP, cellobiose, mannitol, mannose, glucose (dextrose), allose, altrose, gulose, idose, lactose, maltose, dextrose, galactose, talose, psicose, fructose, sorbose, tagatose, β-d-ribopyranose, α-d-ribopyranose, β-d-ribofuranose, α-d-ribofuranose, sucrose, xylose, trehalose, maltodextrins, raffinose, stachyose, fructo-oligosaccharides, amylose, amylopectin, and microcrystalline cellulose, as well as combinations thereof.

In particular (but non-limiting) embodiments of the present disclosure, the highly soluble sugar is selected from the group xylitol, glycerine, dipropylene glycol, glycerol, panthenol, tartaric acid, mannitol, lactose, maltose, dextrose, galactose, fructose, sucrose, xylose, trehalose, raffinose, sucralose, maltodextrins, fructo-oligosaccharides, amylose, amylopectin, starch, hemicellulose, methyl cellulose, methyl ethyl cellulose, pectins, hydrocolloids, isomaltooligosaccharide, and maltodextrin.

Quantitative descriptors of particle size are the projected area diameter, better known as geometric diameter ($d_g$) and its equivalent volume diameter ($d_v$). The $d_g$ of a particle is obtained from two-dimensional images generated by microscopy and represents the diameter of a circular disc with the same projected area as the particle being examined. The $d_v$ is the diameter of a sphere of the same volume to the particle, which is usually determined by laser diffraction or light obscuration methods. Each of these descriptors has limitations, as $d_g$ cannot discriminate the existence of powder aggregates, and as $d_v$ gives no information about primary particle size and morphology. Thus, both descriptors are usually determined for inhalable dry powders, and their difference in magnitude is used to predict if the powder is aggregated, and in some cases, the extent of aggregation. Still, these two dimensions have limited application to particles deposited in the respiratory tract, as they do not account for the density of the particle with respect to its mass, its shape, or their influence when the powder is dispersed in an air stream.

Prior to the present disclosure, there has been no available product of a drug in nanocrystal (NC) form as a powder. Also, there is currently no commercialized inhaled product for treatment of lung cancer or tuberculosis (TB). Additionally, there is no commercialized product comprising SHetA2 or other flexible heteroarotinoids. The compositions of the present disclosure differ from conventional technologies based on (for example, but not by way of limitation) fabrication method, route of delivery, form of the drug, microparticle size and size distribution, and/or lack of toxicity. In one non-limiting embodiment, the NC-MPs are formulated to be inhalable in a mammalian lung.

When NCs are combined with carrier materials to form microparticles (MPs) using the technology disclosed herein, the resulting nanocrystal microparticles (NC-MPs) can significantly increase the dissolution rate of the nanocrystalline drug (particularly of a poorly soluble drug) in the composition, by increasing their saturation solubility, which in turn increases drug absorption, resulting in high concentrations of the drug at the site of delivery. For example (but not by way of limitation), SHetA2 NC-MPs of the present disclosure significantly increase the dissolution rate of drugs by about 4-fold and about 25-fold when compared to amorphous SHetA2 MPs and unprocessed drug, respectively, and increased the saturation solubility by about 4.25-fold and about 15-fold when compared to amorphous SHetA2 MPs and unprocessed drug, respectively. Further, the use of an NC form of the drug increases the stability of the drug at the site of action and the shelf life of a product by decreasing the likelihood of degradation by the microenvironment or storage conditions, respectively.

The presently disclosed NC-MP drug formulations provide the capability of offering up to substantially 100% drug content at the site of action and enable the targeting of different regions of the respiratory tract and lung tissue. In addition, the microparticulate aggregation of the nanoparticles renders them more stable thermodynamically and prevents crystal growth in the microenvironment at the site of drug action.

Use of the presently disclosed NC-based dry powder aerosol formulations disclosed or otherwise contemplated herein allows for decreased dosage size while resulting in, for example (but not by way of limitation), faster dissolution, faster and enhanced absorption, and longer residence time, thereby increasing efficacy of treatment and decreasing side effects.

Certain non-limiting embodiments of the present disclosure are directed to microparticulate drug compositions that comprise microparticles that include NCs of a poorly soluble drug and a carrier (excipient), wherein the carrier is a highly-soluble sugar such as described elsewhere herein.

The NCs may be provided with any size and/or shape that allows the microparticulate drug compositions formed using the NCs to function in accordance with the present disclosure. For example, but not by way of limitation, the nanoparticles may have an average geometric diameter of less than about 2 μm, less than about 1.5 μm, less than about 1.0 μm, less than about 0.9 μm, less than about 0.8 μm, less than about 0.7 μm, less than about 0.6 μm, less than about 0.5 μm, less than about 0.4 μm, less than about 0.3 μm, less than about 0.2 μm, less than about 0.1 μm, less than about 0.09 μm, less than about 0.08 μm, less than about 0.07 μm, less than about 0.06 μm, less than about 0.05 μm, less than about 0.04 μm, less than about 0.03 μm, less than about 0.02 μm, less than about 0.01 μm, and the like. In addition, the average geometric diameter of the NCs may fall within a range of any two of the values listed above, such as (but not limited to), a range of from about 0.01 μm to about 1.0 μm, a range of from about 0.05 μm to about 0.5 μm, and the like.

The MPs comprising the NCs and the carrier material (NC-MPs) may be provided with any size that allows the microparticulate drug compositions to function in accordance with the present disclosure. For example, but not by way of limitation, the NC-MPs may an average geometric diameter of less than about 5 μm, less than about 4 μm, less than about 3.5 μm, less than about 3 μm, less than about 2.9 μm, less than about 2.8 μm, less than about 2.7 μm, less than about 2.6 μm, less than about 2.5 μm, less than about 2.4 μm, less than about 2.3 μm, less than about 2.2 μm, less than about 2.1 μm, less than about 2.0 μm, less than about 1.9 μm, less than about 1.8 μm, less than about 1.7 μm, less than about 1.6 μm, less than about 1.5 μm, less than about 1.4 μm, less than about 1.3 μm, less than about 1.2 μm, less than about 1.1 μm, less than about 1.0 μm, less than about 0.9 μm, less than about 0.8 μm, less than about 0.7 μm, less than about 0.6 μm, less than about 0.5 μm, less than about 0.4 μm, less than about 0.3 μm, less than about 0.2 μm, less than about 0.1 μm, and the like. In addition, the average geometric diameter of the NC-MPs may fall within a range of any two of the values listed above, such as (but not limited to), a range of from about 1.0 μm to about 3.5 μm, a range of from about 2.3 μm to about 2.9 μm, and the like.

In other non-limiting embodiments, the NC-MPs may have an average geometric diameter in a range of about 1 μm to about 500 μm. This range includes, by way of example but not limitation, a subrange of about 1 μm to about 400 μm, a subrange of about 1 μm to about 300 μm, a subrange of about 1 μm to about 200 μm, a subrange of about 1 μm to about 100 μm, a subrange of about 1 μm to about 75 μm, a subrange of about 1 μm to about 50 μm, a subrange of about 1 μm to about 30 μm, a subrange of about 1 μm to about 25 μm, a subrange of about 1 μm to about 20 μm, a subrange of about 1 μm to about 15 μm, a subrange of about 1 μm to about 10 μm, and a subrange of about 1 μm to about 5. In addition, the average geometric diameter of the NC-MPs may fall within a range of any two of the values listed above, such as (but not limited to), a range of from about 25 μm to about 150 μm, a range of from about 10 μm to about 50 μm, a range of from about 100 μm to about 500, μm, and the like.

In certain non-limiting embodiments of the present disclosure, the dry powder formulation is a dry powder aerosol formulation that can be used for pulmonary administration or nasal administration. Average geometric diameters of the microparticles are typically in a range of about 1 μm to about 5 μm for pulmonary administration, and are typically in a range of about 20 μm to about 40 μm for nasal administration.

In addition, the NC-MPs may have any shape that allows the microparticulate drug compositions to function as described herein. For example (but not by way of limitation), the NC-MPs may have an average volume diameter of less than about 10 μm, less than about 9 μm, less than about 8 μm, less than about 7 μm, less than about 6 μm, less than about 5 μm, less than about 4 μm, less than about 3.9 μm, less than about 3.8 μm, less than about 3.7 μm, less than about 3.6 μm, less than about 3.5 μm, less than about 3.4 μm, less than about 3.3 μm, less than about 3.2 μm, less than about 3.1 μm, less than about 3.0 μm, less than about 2.9 μm, less than about 2.8 μm, less than about 2.7 μm, less than about 2.6 μm, less than about 2.5 μm, less than about 2.4 μm, less than about 2.3 μm, less than about 2.2 μm, less than about 2.1 μm, less than about 2.0 μm, less than about 1.9 μm, less than about 1.8 μm, less than about 1.7 μm, less than about 1.6 μm, less than about 1.5 μm, less than about 1.4 μm, less than about 1.3 μm, less than about 1.2 μm, less than about 1.1 μm, less than about 1.0 μm, less than about 0.9 μm, less than about 0.8 μm, less than about 0.7 μm, less than about 0.6 μm, less than about 0.5 μm, less than about 0.4 μm, less than about 0.3 μm, less than about 0.2 μm, less than about 0.1 μm, and the like. In addition, the average volume diameter of the NC-MPs may fall within a range of any two of the values listed above, such as (but not limited to), a range of from about 3 μm to about 5 μm, a range of from about 5 μm to about 10 μm, and the like.

In other non-limiting embodiments, the NC-MPs may have an average volume diameter in a range of about 1 μm to about 500 μm. This range includes, by way of example but not limitation, a subrange of about 1 μm to about 400 μm, a subrange of about 1 μm to about 300 μm, a subrange of about 1 μm to about 200 μm, a subrange of about 1 μm to about 100 μm, a subrange of about 1 μm to about 75 μm, a subrange of about 1 μm to about 50 μm, a subrange of about 1 μm to about 30 μm, a subrange of about 1 μm to about 25 μm, a subrange of about 1 μm to about 20 μm, a subrange of about 1 μm to about 15 μm, a subrange of about 1 μm to about 10 μm, and a subrange of about 1 μm to about 5. In addition, the average volume diameter of the NC-MPs may fall within a range of any two of the values listed above, such as (but not limited to), a range of from about 25 μm to about 150 μm, a range of from about 10 μm to about 50 μm, a range of from about 100 μm to about 500, μm, and the like.

In one particular (but non-limiting) embodiment, the NCs have an average geometric diameter less than about 0.2 μm, and the NC-MPs have an average geometric diameter of less than about 2.7 μm and an average volume diameter of less than about 3.1 μm.

In certain non-limiting embodiments, the ratio of average volume diameter to average geometric diameter (i.e., $d_v/d_g$ ratio) of the NC-MPs of the present disclosure is in a range of from about 1 to about 10, such as (but not limited to), a range of from about 1 to about 9, a range of from about 1 to about 8, a range of from about 1 to about 7, a range of from about 1 to about 6, a range of from about 1 to about 5, a range of from about 1 to about 4, a range of from about 1 to about 3.5, a range of from about 1 to about 3, a range of from about 1 to about 2.5, a range of from about 1 to about 2, a range of from about 1.0 to about 1.5, and the like.

The active agent of the NC-MPs of the present disclosure may be any poorly soluble drug as defined or otherwise contemplated herein. One non-limiting class of poorly soluble drugs that may be utilized in accordance with the present disclosure are heteroarotinoids; non-limiting examples of heteroarotinoids that may be used as the active agent include (but are not limited to) any heteroarotinoid disclosed in U.S. Pat. No. 6,586,460 (see, for example, Columns 2-5 thereof) and U.S. Pat. No. 7,612,107 (see, for example, Columns 7-9 thereof). Particular non-limiting examples of heteroarotinoids that can be used as the active agent include SHetA2, SHetA3, SHetA4, SHetC2, SHetD3, SHetD4, SHetD5, SHet50, SHet65, SHet100, OHet72, NHet17, NHet86, NHet90, heteroarotinoid compounds shown in Table 1, compounds 1-3 shown in Table 2, heteroarotinoid compounds shown in Table 3, heteroarotinoid compounds shown in Table 4, heteroarotinoid compounds shown in Table 5, heteroarotinoid compounds shown in Table 6, heteroarotinoid compounds shown in Table 7, and heteroarotinoid compounds shown in Table 8.

TABLE 1

| Heteroarotinoids (Benbrook et al., 1997*) | | | |
|---|---|---|---|
| 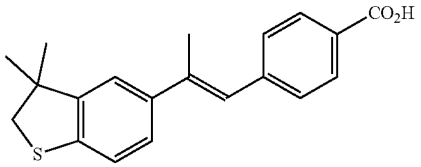 [SMILES: C/C(=C\c1ccc(C(=O)O)cc1)c1ccc2c(c1)C(C)(C)CS2] 11 | 56 | 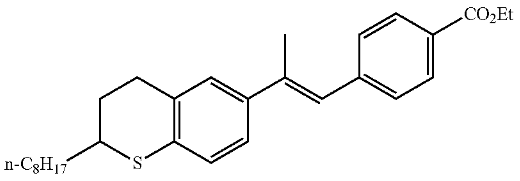 16 | 43 |
| 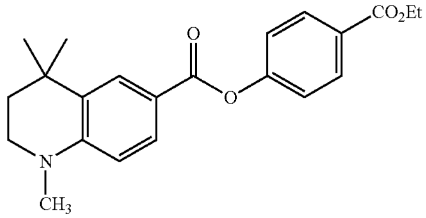 [SMILES: CCOC(=O)c1ccc(OC(=O)c2ccc3c(c2)C(C)(C)CCN3C)cc1] 19 | 54 | 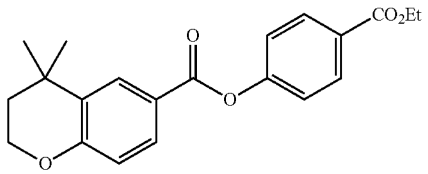 [SMILES: CCOC(=O)c1ccc(OC(=O)c2ccc3c(c2)C(C)(C)CCO3)cc1] 18 | 40 |
| 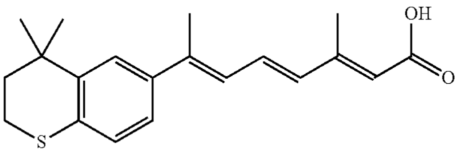 [SMILES: CC(/C=C/C=C(\C)c1ccc2c(c1)C(C)(C)CCS2)=C\C(=O)O] 8 | 52 | 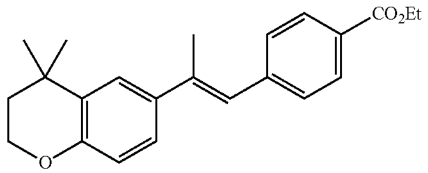 14 | 35.7 |
| 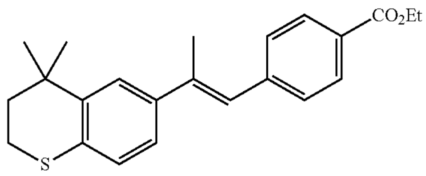 [SMILES: CCOC(=O)c1ccc(/C=C(\C)c2ccc3c(c2)C(C)(C)CCO3)cc1] 15 | 51 | 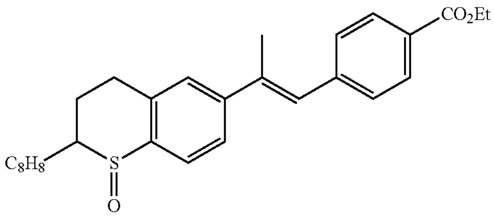 17 | 35.8 |
| 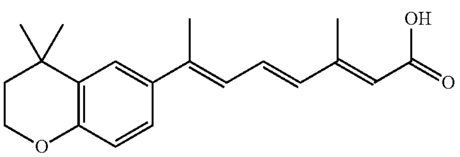 [SMILES: CC(/C=C/C=C(\C)c1ccc2c(c1)C(C)(C)CCO2)=C\C(=O)O] 10 | 50 | 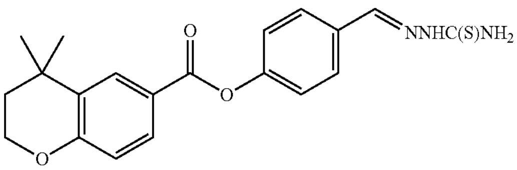 20 | 33 |

TABLE 1-continued
Heteroarotinoids (Benbrook et al., 1997*)
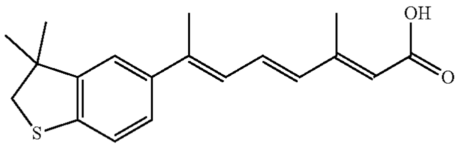 [SMILES: CC(/C=C/C=C(\C)c1ccc2c(c1)C(C)(C)CS2)=C\C(=O)O]
50
12
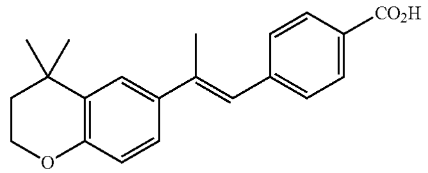 [SMILES: C/C(=C\c1ccc(C(=O)O)cc1)c1ccc2c(c1)C(C)(C)CCO2]
31
13
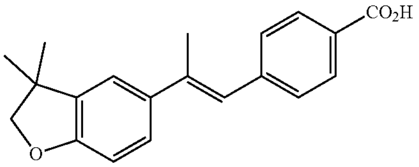 [SMILES: C/C(=C\c1ccc(C(=O)O)cc1)c1ccc2c(c1)C(C)(C)CO2]
46
9
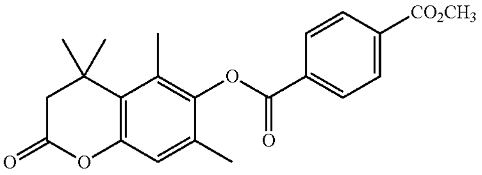 [SMILES: COC(=O)c1ccc(C(=O)Oc2c(C)cc3c(c2C)C(C)(C)CC(=O)O3)cc1]
29
21
*D. M. Benbrook et al., "Biologically Active Heteroarotinoids Exhibiting Anticancer Activity and Decreased Toxicity," J. Med. Chem., 1977, 40 (3567-3583).
TABLE 2
Nitrogen Heteroarotinoids (Dhar et al., 1999*)
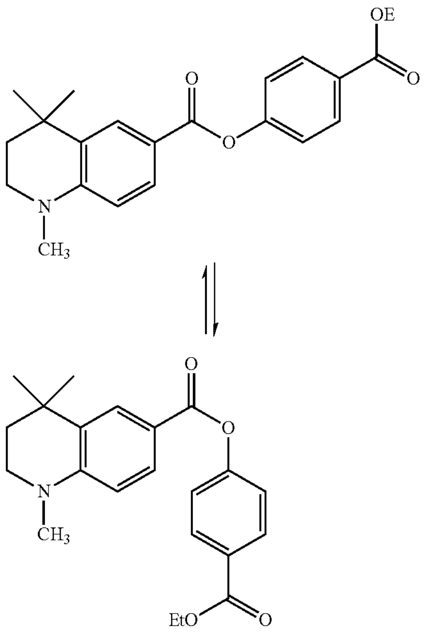
1
TABLE 2-continued
Nitrogen Heteroarotinoids (Dhar et al., 1999*)
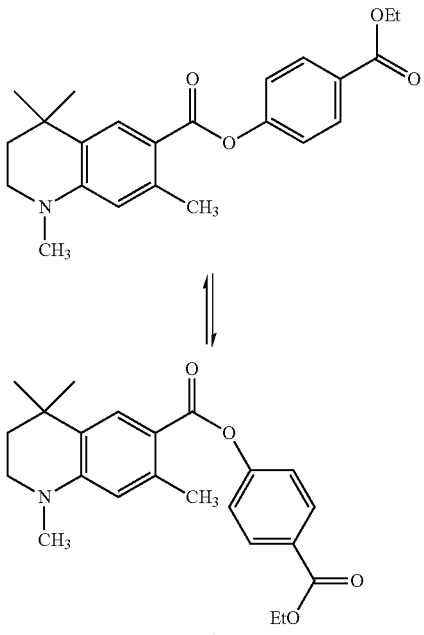 [SMILES: CCOC(=O)c1ccc(OC(=O)c2cc3c(cc2C)N(C)CCC3(C)C)cc1 ; CCOC(=O)c1ccc(OC(=O)c2cc3c(cc2C)N(C)CCC3(C)C)cc1]
2

TABLE 2-continued
Nitrogen Heteroarotinoids (Dhar et al., 1999*)
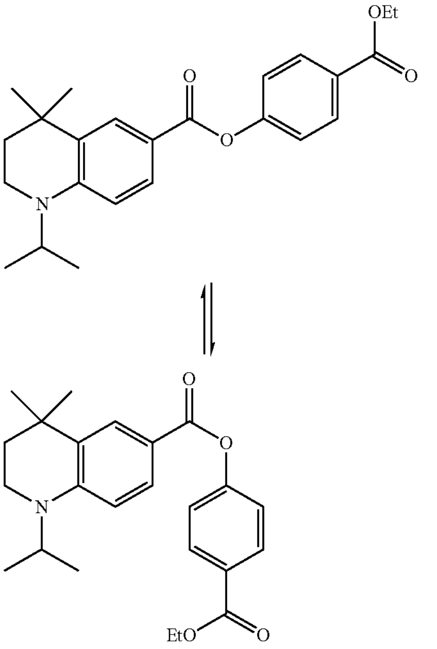 [SMILES: CCOC(=O)c1ccc(OC(=O)c2ccc3c(c2)C(C)(C)CCN3C(C)C)cc1 ; CCOC(=O)c1ccc(OC(=O)c2ccc3c(c2)C(C)(C)CCN3C(C)C)cc1]
3
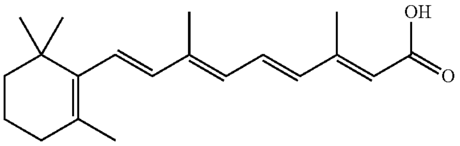 [SMILES: CC1=C(/C=C/C(C)=C/C=C/C(C)=C/C(=O)O)C(C)(C)CCC1]
t-RA
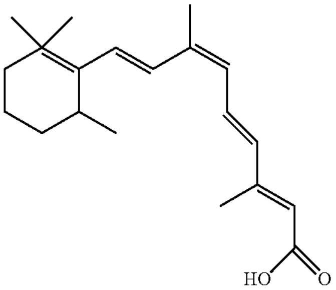
9-c-RA
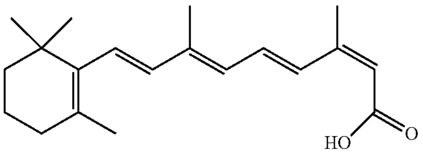 [SMILES: CC1=C(/C=C/C(C)=C/C=C/C(C)=C\C(=O)O)C(C)(C)CCC1]
13-c-RA
TABLE 2-continued
Nitrogen Heteroarotinoids (Dhar et al., 1999*)
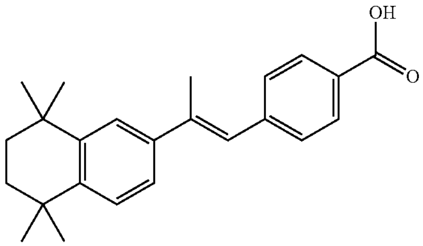
TTNBP
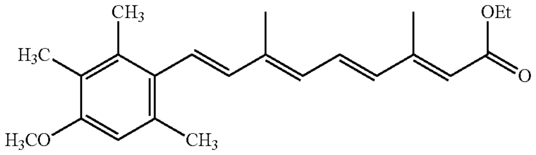
Etretinate
*A. Dhar et al., "Synthesis, Structure-Activity Relationships, and RARγ-Ligand Interactions of Nitrogen Heteroarotinoids," J. Med. Chem., 1999, 42 (3602-3614).
TABLE 3
Heteroarotinoids (Zacheis et al., 1997*)
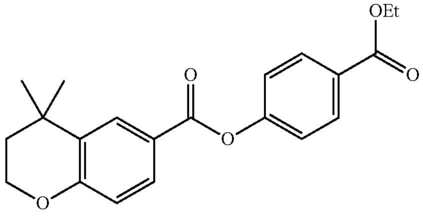
5
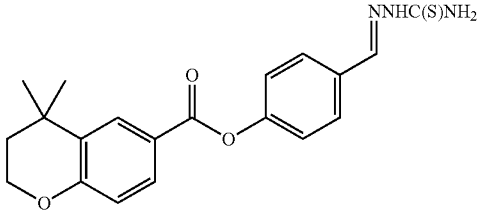
6
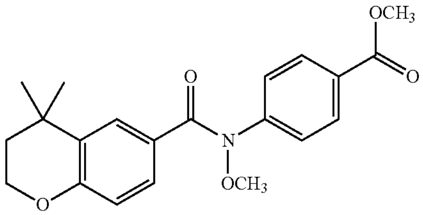
7

TABLE 3-continued
| Heteroarotinoids (Zacheis et al., 1997*) |
|---|
| 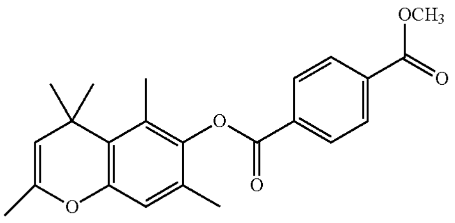 |
| 8 |
| 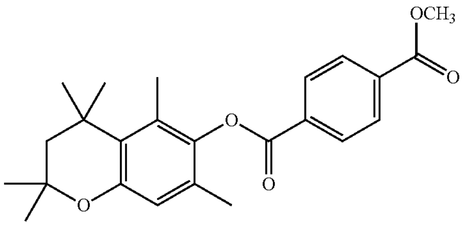 |
| 9 |
| 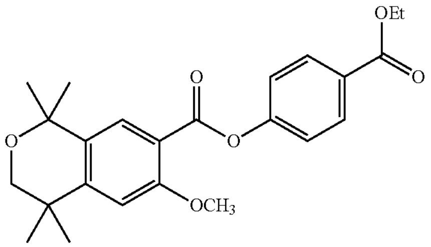 |
| 10 |
| 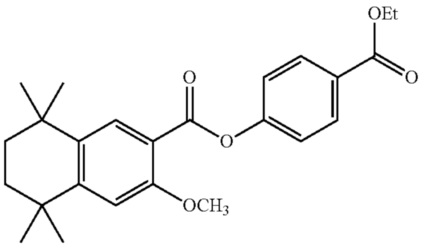 [SMILES: CCOC(=O)c1ccc(OC(=O)c2ccc3c(c2)C(C)(C)CCO3)cc1] |
| 11 |
| 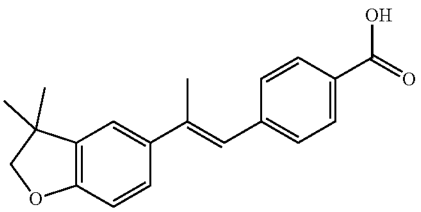 |
| 12 |
TABLE 3-continued
| Heteroarotinoids (Zacheis et al., 1997*) |
|---|
| 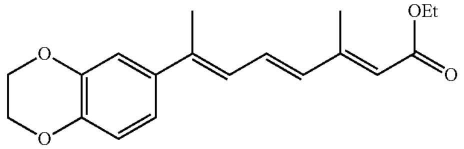 |
| 13 |
| 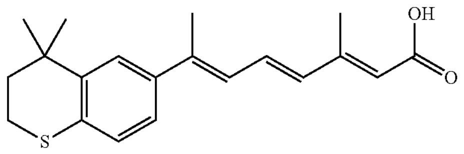 |
| 14 |
| 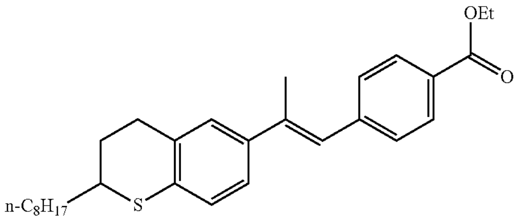 |
| 15 |
| 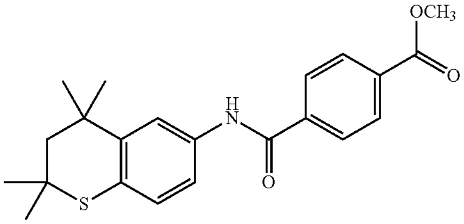 |
| 16 |
| 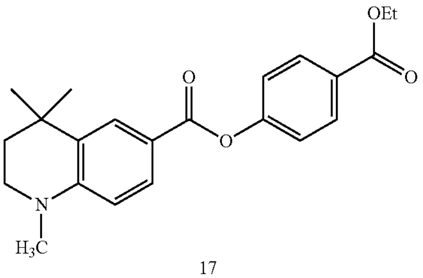 [SMILES: CCOC(=O)c1ccc(OC(=O)c2ccc3c(c2)C(C)(C)CCN3C)cc1] |
| 17 |

TABLE 3-continued
| Heteroarotinoids (Zacheis et al., 1997*) |
|---|
| 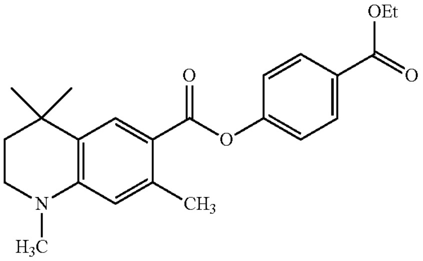<br>18 |
| 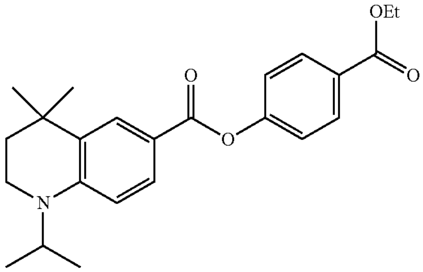<br>19 |
*D. Zacheis et al., "Heteroarotinoids Inhibit Head and Neck Cancer Cell Lines in Vitro and in Vivo Through Both RAR and RXR Retinoic Acid Receptors," J. Med. Chem., 1999, 42 (4434-4445).
TABLE 4
| Heteroarotinoids (Brown et al., 2004*) | |
|---|---|
| 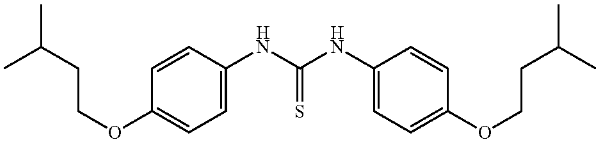<br>7 [Isoxyl] | 0.5-1.0 |
| 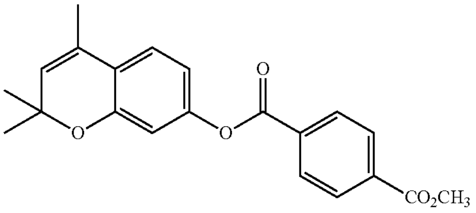<br>8 | 2.0-4.0 |
| 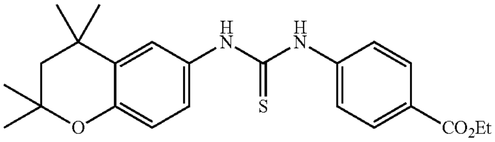<br>9 | 5.0-10.0 |
| 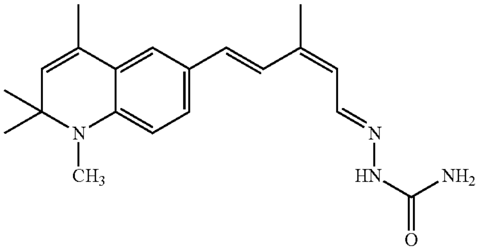<br>10 | 10.0-20.0 |

TABLE 4-continued
| Heteroarotinoids (Brown et al., 2004*) | |
|---|---|
| 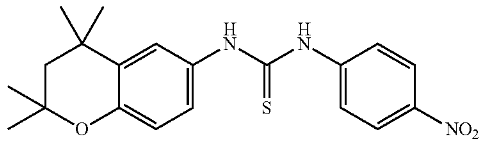 11 | 20.0-40.0 |
| 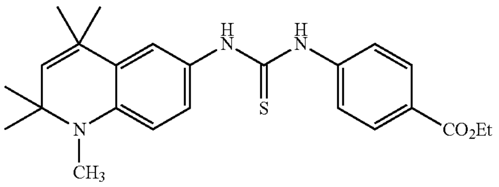 12 | 20.0-40.0 |
| 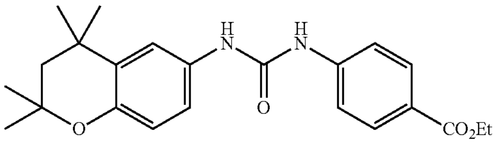 13 | 20.0-40.0 |
| 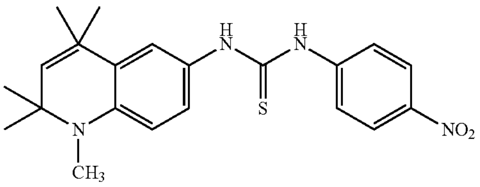 14 | 20.0-40.0 |
| 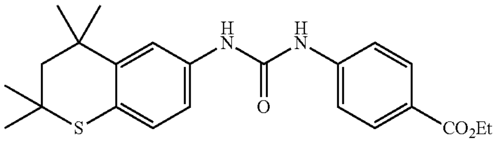 15 | 20.0-40.0 |
| 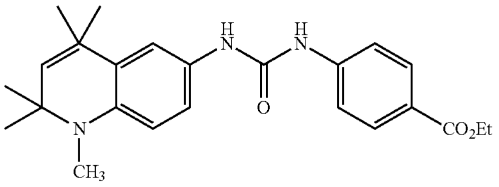 16 | 20.0-40.0 |
| 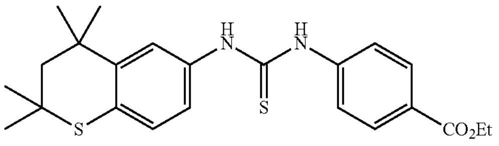 17 | 20.0-40.0 |

TABLE 4-continued
| Heteroarotinoids (Brown et al., 2004*) | |
|---|---|
| 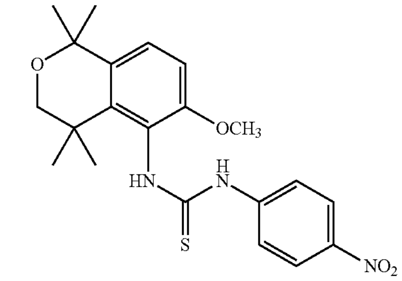<br>18 | 20.0-40.0 |
| 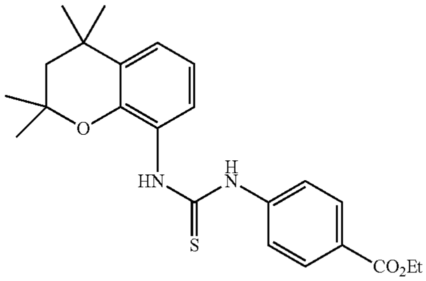<br>19 | 20.0-40.0 |
| 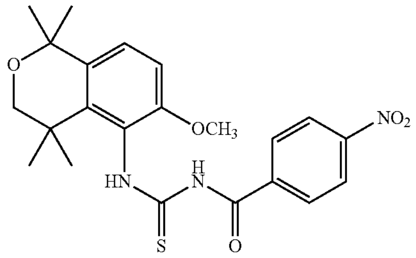<br>20 | 20.0-40.0 |
| 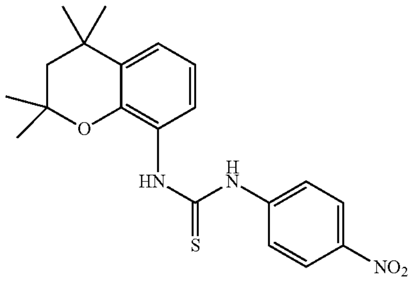<br>21 | 20.0-40.0 |

TABLE 4-continued

| Heteroarotinoids (Brown et al., 2004*) | |
|---|---|
| 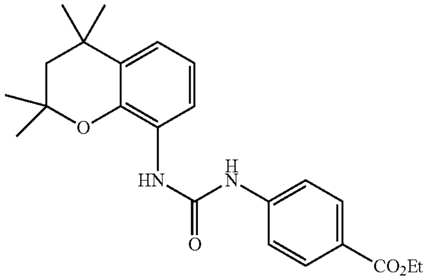<br>22 | 20.0-40.0 |

*C. W. Brown et al., "Novel Heteroarotinoids as Potential Antagonists of *Mycobacterium bovis* BCG," J. Med. Chem., 2004, 47 (1008-1017).

TABLE 5

Heteroarotinoids (Le et al., 2007*)

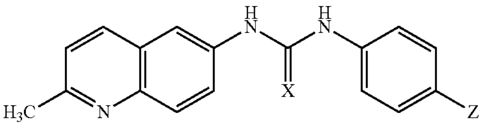

9 a. X = S; Z = $NO_2$
b. X = O; Z = $NO_2$
c. X = O; Z = $CO_2Et$

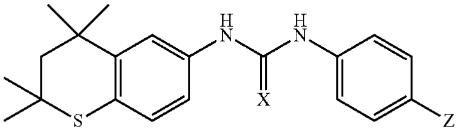

10 a. X = S; Z = $NO_2$
b. X = S; Z = $CO_2Et$
c. X = O; Z = $NO_2$
d. X = O; Z = $CO_2Et$

*T. C. Le et al., "Heteroarotinoids with Anti-Cancer Activity Against Ovarian Cancer Cells," The Open Medicinal Chemistry Journal, 2007, 1 (11-23).

TABLE 6

Heteroarotinoids (Liu et al., 2004*)

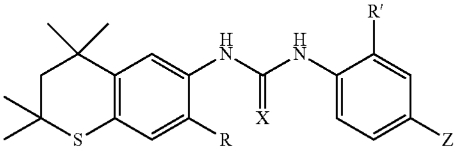

15a-h

| entry | R | X | R | Z | product | yield (%) |
|---|---|---|---|---|---|---|
| 1 | H | O | H | $CO_2Et$ | 15a | 64 |
| 2 | H | S | H | $CO_2Et$ | 15b | 92 |
| 3 | H | S | H | $NO_2$ | 15c | 83 |
| 4 | H | S | H | $SO_2NH_2$ | 15d | 87 |
| 5 | H | S | $CH_3$ | $NO_2$ | 15e | 82 |
| 6 | $CH_3$ | O | H | $CO_2Et$ | 15f | 43 |

TABLE 6-continued

Heteroarotinoids (Liu et al., 2004*)

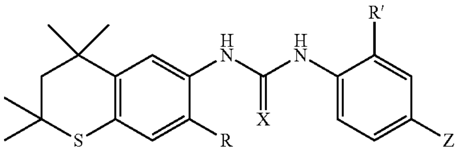

15a-h

| entry | R | X | R | Z | product | yield (%) |
|---|---|---|---|---|---|---|
| 7 | $CH_3$ | S | H | $CO_2Et$ | 15g | 66 |
| 8 | $CH_3$ | S | H | $SO_2NH_2$ | 15h | 56 |

*S. Liu et al., "Synthesis of Flexible Sulfur-Containing Heteroarotinoids That Induce Apoptosis and Reactive Oxygen Species with Discrimination between Malignant and Benign Cells," J. Med. Chem., 2004, 47 (999-1007).

TABLE 7

Heteroarotinoids (Gnanasekaran et al., 2015*)

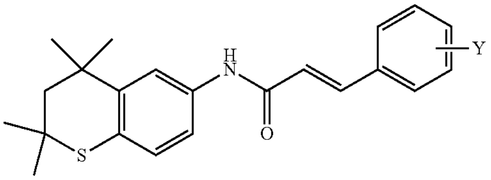

18a-h
20a-c

| Compound | Y |
|---|---|
| Nitrogen-Substituted Flex-Hets | |
| 5 (SHetA2) | 4-$NO_2$ |
| 18b | 4-$NO_2$ |
| 18f | 4-$N(CH_3)_2$ |
| 18h | 4-$NH_2$ |
| 20a | 4-N-methylamide |
| 20b | 4-N-cyclopropylamide |
| 20c | 4-oxomorpholino |
| Non-Nitrogen-Substituted Flex-Hets | |
| 18a | 4-$CO_2Et$ |
| 18c | 4-$CF_3$ |
| 18d | 2,3,4,5,6-F |

TABLE 7-continued

Heteroarotinoids (Gnanasekaran et al., 2015*)

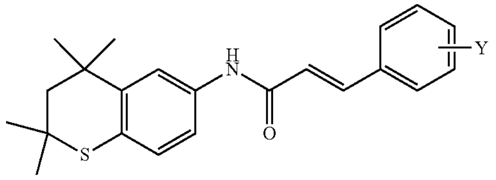

18a-h
20a-c

| Compound | Y |
|---|---|
| 18e | 3,4-$OCH_3$ |
| 18g | 4-$CO_2H$ |

*K. K. Gnanasekaran et al., "Synthesis and evalution of second generation Flex-Het scaffolds against the human ovarian A2780 cancer cell line," European J. Med. Chem., 2015, 96 (209-217).

TABLE 8

| Heteroarotinoids (Liu et al., 2009*) | |
|---|---|
| 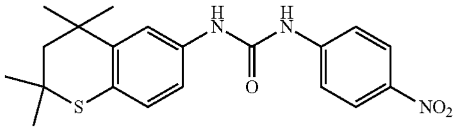 [SMILES: CC1(C)CC(C)(C)c2cc(NC(=O)Nc3ccc([N+](=O)[O-])cc3)ccc2S1] | SHetC2 |
| 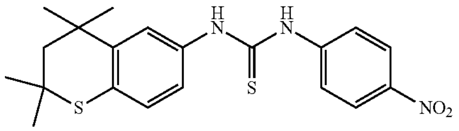 [SMILES: CC1(C)CC(C)(C)c2cc(NC(=S)Nc3ccc([N+](=O)[O-])cc3)ccc2S1] | SHetA2 |
| 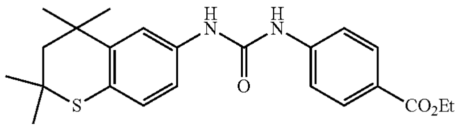 [SMILES: CCOC(=O)c1ccc(NC(=O)Nc2ccc3c(c2)C(C)(C)CC(C)(C)S3)cc1] | SHetA4 |
| 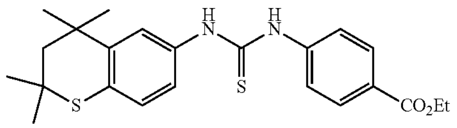 | SHetA3 |
| 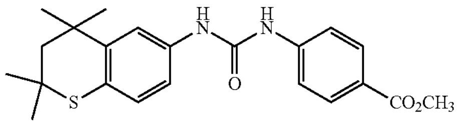 | SHetD3 |
| 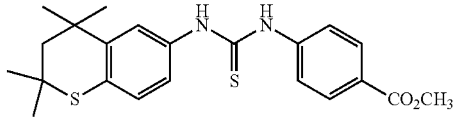 [SMILES: COC(=O)c1ccc(NC(=O)Nc2ccc3c(c2)C(C)(C)CC(C)(C)S3)cc1] | SHetD4 |
| 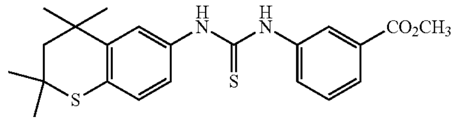 [SMILES: COC(=O)c1cccc(NC(=S)Nc2ccc3c(c2)C(C)(C)CC(C)(C)S3)c1] | SHetD5 |

*T. Liu et al., "Development of flexible-heteroarotinoids for kidney cancer," Mol. Cancer Ther., 2009, 8(5), (1227-1238).

TABLE 9

| Clofazimine (CFM) and riminophenazine analogs (Y. Lu et al., 2011*) | |
|---|---|
| TBI-161 | 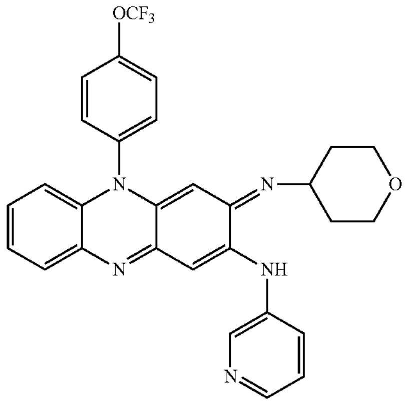 [SMILES: FC(F)(F)Oc1ccc(-n2c3c/c(=N/C4CCOCC4)c(Nc4cccnc4)cc-3nc3ccccc32)cc1] |
| TBI-166 | 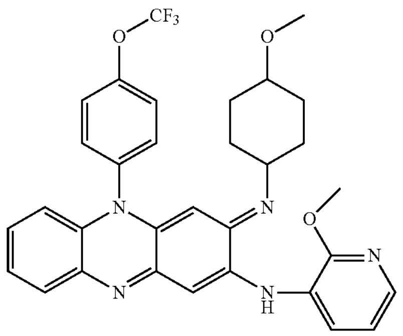 [SMILES: COc1ncccc1Nc1cc2nc3ccccc3n(-c3ccc(OC(F)(F)F)cc3)c-2c/c1=N\C1CCC(OC)CC1] |
| TBI-416 | 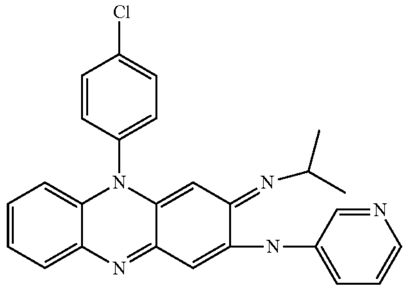 [SMILES: CC(C)/N=c1/cc2n(-c3ccc(Cl)cc3)c3ccccc3nc-2cc1Nc1cccnc1] |
| TBI-443 | 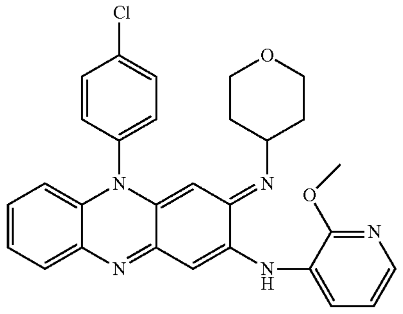 [SMILES: COc1ncccc1Nc1cc2nc3ccccc3n(-c3ccc(Cl)cc3)c-2c/c1=N\C1CCOCC1] |

TABLE 9-continued

| Clofazimine (CFM) and riminophenazine analogs (Y. Lu et al., 2011*) | |
|---|---|
| TBI-444 | 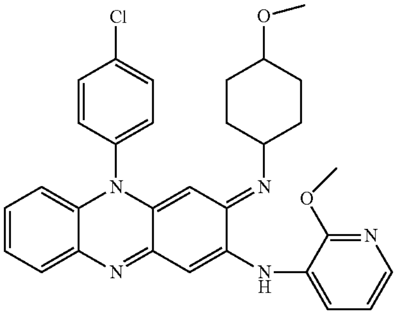 [SMILES: COc1ncccc1Nc1cc2nc3ccccc3n(-c3ccc(Cl)cc3)c-2c/c1=N\C1CCC(OC)CC1] |
| TBI-449 | 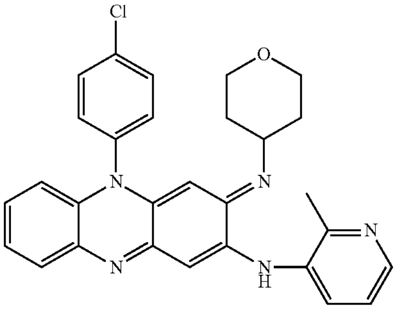 [SMILES: Cc1ncccc1Nc1cc2nc3ccccc3n(-c3ccc(Cl)cc3)c-2c/c1=N\C1CCOCC1] |
| TBI-450 | 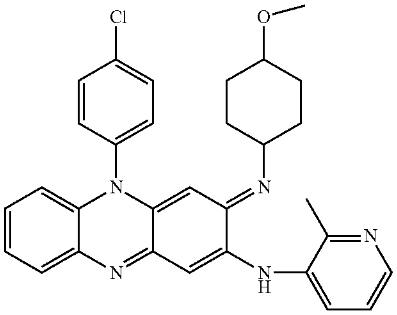 [SMILES: COC1CCC(/N=c2\cc3n(-c4ccc(Cl)cc4)c4ccccc4nc-3cc2Nc2cccnc2C)CC1] |
| TBI-678 | 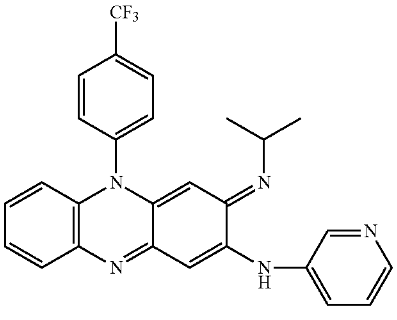 [SMILES: CC(C)/N=c1\cc2n(-c3ccc(C(F)(F)F)cc3)c3ccccc3nc-2cc1Nc1cccnc1] |
| TBI-688 | 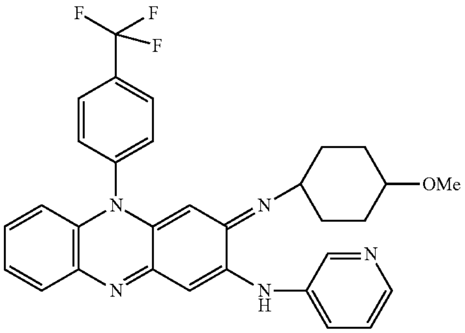 [SMILES: COC1CCC(N=c2cc3n(-c4ccc(C(F)(F)F)cc4)c4ccccc4nc-3cc2Nc2cccnc2)CC1] |

TABLE 9-continued

| Clofazimine (CFM) and riminophenazine analogs (Y. Lu et al., 2011*) | |
|---|---|
| TBI-1002 | 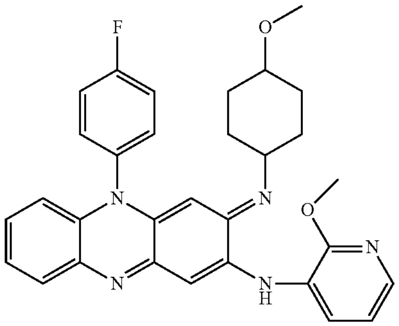 [SMILES: COc1ncccc1Nc1cc2nc3ccccc3n(-c3ccc(F)cc3)c-2c/c1=N\C1CCC(OC)CC1] |
| TBI-1004 | 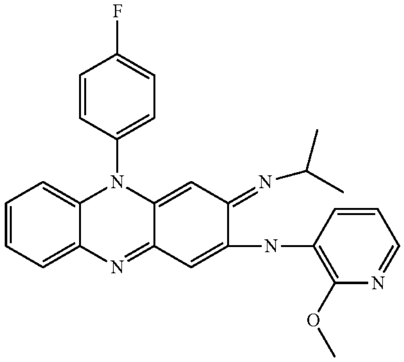 [SMILES: COc1ncccc1Nc1cc2nc3ccccc3n(-c3ccc(F)cc3)c-2c/c1=N/C(C)C] |
| TBI-1010 | 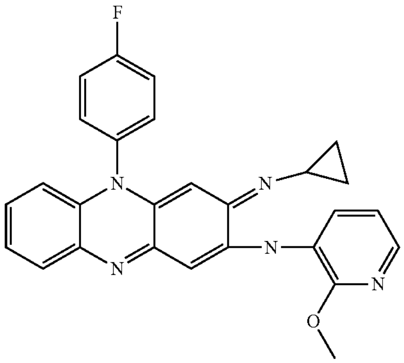 [SMILES: COc1ncccc1Nc1cc2nc3ccccc3n(-c3ccc(F)cc3)c-2c/c1=N/C1CC1] |
| CFM | 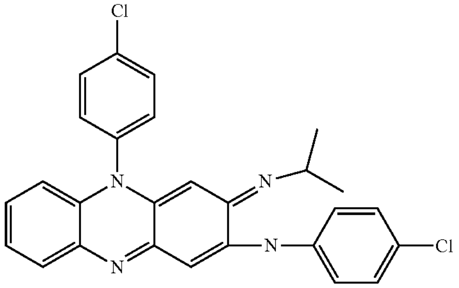 [SMILES: CC(C)/N=c1/cc2n(-c3ccc(Cl)cc3)c3ccccc3nc-2cc1Nc1ccc(Cl)cc1] |

*Y. Lu et al., "Clofazimine analogs with Efficacy Against Experimental Tuberculosis and Reduced Potential for Accumulation," Antimicrob Agents Chemother. 2011, 55 (5185-5193).

In certain non-limiting embodiments, the active agent that comprises the nanocrystals may be a cyclin-dependent kinase 4 and 6 (CDK4/6) inhibitor such as, but not limited to, Palbociclib, Abemaciclib, Ribociclib, and/or ON123300. Other CDK4/6 inhibitors are disclosed in US Published Patent Application Nos. US 2014/0227222, US 2017/0246171, and/or US 2019/0209566.

In certain non-limiting embodiments, the active agent that comprises the nanocrystals may be a poly-ADP-ribose polymerase WARP) inhibitor such as, but not limited to, Olaparib, Niraparib, Rucaparib, Talazoparib, Veliparib, Pamiparib, BMN673, CEP 9722, and/or E7016.

In certain non-limiting embodiments, the active agent that comprises the nanocrystals may be an Azabicyclooctan-3-one derivative, such as PRIMA-1, PRIMA-$1^{MET}$, and analogs thereof shown in International Patent Application Publication Nos. WO 2002/024692 and WO 2003/070250, and/or U.S. Pat. No. 7,759,361.

In certain non-limiting embodiments, the active agent that comprises the nanocrystals may be a riminophenazine analog which has inhibitory activity against *Mycobacterium tuberculosis*, such as TBI-161, TBI-166, TBI-416, TBI-443, TBI-444, TBI-449, TBI-450, TBI-678, TBI-688, TBI-1002, TBI-1004, TBI-1010, and/or clofazimine.

In certain embodiments the active agent that comprises the nanocrystals is rifamycin or a rifamycin derivative. In certain embodiments the rifamycin derivative is selected from rifampicin, rifabutin, and rifapentine.

In certain embodiments the active agent that comprises the nanocrystals is selected from isoxyl, thiacetazone, ethionamide, isoniazid.

Where used herein the term "cancer," "cancer cell," or "tumor" can be used in reference to various cancers including, but not limited to, ovarian cancer, cervical cancer, peritoneal cancer, uterine cancer, vulvar cancer, oral cancer, pharyngeal cancer, oropharyngeal cancer, nasopharyngeal cancer, lung cancer, urogenital cancer, gastrointestinal cancer, central or peripheral nervous system tissue cancer, an endocrine cancer, neuroendocrine cancer, glioma, carcinoma, lymphoma, melanoma, fibroma, meningioma, brain cancer, renal cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, head and neck cancer, prostate cancer, esophageal cancer, tracheal cancer, liver cancer, bladder cancer, stomach cancer, pancreatic cancer, uterine cancer, testicular cancer, colon cancer, rectal cancer, and skin cancer, and any other cancer which comprises one or more mutations in the TP53 gene or which is driven by the cyclin D1/cdk4/6 complex.

In other non-limiting embodiments, the term "cancer," "cancer cell," or "tumor" can be used in reference to various cancers including, but not limited to, breast cancer (e.g., estrogen receptor positive or negative, progesterone receptor positive or negative, HER-2 positive or negative, triple-negative breast cancer, or BRCA1 and/or BRCA2 positive or negative), lung cancer (e.g., non-small cell lung cancer and small cell lung cancer), endometrial cancer, glioblastoma, B-cell malignancies, biliary tract cancer, bone cancer, choriocarcinoma, connective tissue cancer, cancers of the digestive system, gallbladder cancer, hepatocellular carcinoma, intra-epithelial neoplasm, kidney cancer, liver cancer, lymphoma, skin cancer (e.g., melanoma and basal cell carcinoma), neuroblastoma, mesothelioma, neuroglioma, oral cavity cancer, pediatric cancer, pancreatic endocrine tumors, pituitary adenoma, thymoma, renal cell carcinoma, salivary gland cancer, sarcoma (e.g., Ewing's sarcoma, fibrosarcoma, and rhabdomyosarcoma), small bowel cancer, ureteral cancer, cancers of the urinary system, and hematological cancers (e.g., acute myeloid leukemia and multiple myeloma).

Exemplary solid cancerous tumors that can be treated with the active agents of the present disclosure include, but are not limited to, a tumor of an organ selected from the group consisting of pancreas, colon, cecum, stomach, brain, liver, gallbladder, head, neck, ovary, kidney, larynx, sarcoma, lung, bladder, uterus, melanoma, prostate, and breast Exemplary hematological tumors include tumors of the bone marrow. T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated, giant and spindle cell carcinoma; small cell carcinoma; papillary carcinoma; squamous cell carcinoma; lymphoepithelial carcinoma, basal cell carcinoma, pilomatrix carcinoma, transitional cell carcinoma; papillary transitional cell carcinoma: adenocarcinoma: gastrinoma, malignant; cholangiocarcinoma; hepatocellular carcinoma; combined hepatocellular carcinoma and cholangiocarcinoma: trabecular adenocarcinoma: adenoid cystic carcinoma: adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma, acidophil carcinoma; oxyphilic adenocarcinoma; basophil carcinoma; clear cell adenocarcinoma, granular cell carcinoma; follicular adenocarcinoma, papillary and follicular adenocarcinoma; nonencapsulating sclerosing carcinoma; adrenal cortical carcinoma; endometroid carcinoma; skin appendage carcinoma, apocrine adenocarcinoma; sebaceous adenocarcinoma; ceruminous adenocarcinoma: mucoepidermoid carcinoma; cystadenocarcinoma; papillary cystadenocarcinoma, papillary serous cystadenocarcinoma, mucinous cystadenocarcinoma; mucinous adenocarcinoma; signet ring cell carcinoma; infiltrating duct carcinoma; medullary carcinoma: lobular carcinoma; inflammatory carcinoma, paget's disease, mammary: acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant: paraganglioma, malignant; extra-mammary paraganglioma, malignant; pheochromocytoma; glomangiosarcoma; malignant melanoma; amelanotic melanoma; superficial spreading melanoma; lentigo malignant melanoma: acral lentiginous melanomas, nodular melanomas, malignant melanoma in giant pigmented nevus, epithelioid cell melanoma: blue nevus, malignant; sarcoma: fibrosarcoma; fibrous histiocytoma, malignant; myxosarcoma; liposarcoma; leiomyosarcoma, rhabdomyosarcoma: embryonal rhabdomyosarcoma: alveolar rhabdomyosarcoma; stromal sarcoma; mixed tumor, malignant; mullerian mixed tumor; nephroblastoma; hepatoblastoma; carcinosarcoma; mesenchymoma, malignant, brenner tumor, malignant; phyllodes tumor, malignant; synovial sarcoma, mesothelioma, malignant; dysgerminoma; embryonal carcinoma; teratoma, malignant; struma ovarii, malignant; choriocarcinoma; mesonephroma, malignant; hemangiosarcoma;

hemangioendothelioma, malignant; Kaposi's sarcoma; hemangiopericytoma, malignant; lymphangiosarcoma; osteosarcoma; juxtacortical osteosarcoma; chondrosarcoma, chondroblastoma, malignant: mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant: ependymoma; astrocytoma; protoplasmic astrocytoma; fibrillary astrocytoma; astroblastoma; glioblastoma, oligodendroglioma; oligodendroblastoma; primitive neuroectodermal; cerebellar sarcoma; ganglioneuroblastoma, neuroblastoma, retinoblastoma; olfactory neurogenic tumor, meningioma, malignant; neurofibrosarcoma; neurilemmoma, malignant: granular cell tumor, malignant; malignant lymphoma; hodgkin's disease, hodgkin's; paragranuloma; malignant lymphoma, small lymphocytic; malignant lymphoma, large cell, diffuse, malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL: high grade immunoblastic NHL; high grade lymphoblastic NHL; high grade small non-cleaved cell NHL; bulky disease NHL; mantle cell lymphoma, AIDS-related lymphoma: Waldenstrom's macroglobulinemia: malignant histiocytosis; multiple myeloma; mast cell sarcoma; immunoproliferative small intestinal disease; leukemia; lymphoid leukemia; plasma cell leukemia; erythroleukemia: lymphosarcoma cell leukemia; myeloid leukemia; basophilic leukemia; eosinophilic leukemia; monocytic leukemia; mast cell leukemia; megakaryoblastic leukemia, myeloid sarcoma, hairy cell leukemia; chronic lymphocytic leukemia (CLL); acute lymphoblastic leukemia (ALL); acute myeloid leukemia (AML): and chronic myeloblastic leukemia.

The microparticulate drug compositions (i.e., NC-MPs) of the present disclosure may be formulated for administration via any of the mechanisms disclosed herein. The microparticulate drug compositions of the present disclosure possess apparent solubilities, saturation solubilities, and/or dissolution rates that are increased over that of an unprocessed form of the drug. For example (but not by way of limitation), the apparent solubility, saturation solubility, and/or dissolution rate of the microparticulate drug composition may be increased when compared to the apparent solubility, saturation solubility, and/or dissolution rate of an unprocessed form of the poorly soluble drug by a factor of at least about 1.25-fold, at least about 1.5-fold, at least about 1.75-fold, at least about 2-fold, at least about 2.25-fold, at least about 2.5-fold, at least about 2.75-fold, at least about 3-fold, at least about 3.25-fold, at least about 3.5-fold, at least about 3.75-fold, at least about 4-fold, at least about 4.25-fold, at least about 4.5-fold, at least about 4.75-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 11-fold, at least about 12-fold, and at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, at least about 30-fold, or higher. In addition, the apparent solubility, saturation solubility, and/or dissolution rate of the microparticulate drug composition may be increased by a factor that falls within a range of any two of the values listed above, such as (but not limited to), a range of from about 2-fold to about 5-fold, a range of from about 10-fold to about 25-fold, and the like.

Similarly, the microparticulate drug compositions of the present disclosure possess apparent solubilities, saturation solubilities, and dissolution rates that are increased over that of a microparticulate amorphous form of the poorly soluble drug. For example (but not by way of limitation), the apparent solubility, saturation solubility, and/or dissolution rate of the microparticulate drug composition may be increased when compared to the apparent solubility, saturation solubility, and/or dissolution rate of a microparticulate amorphous form of the poorly soluble drug by a factor of at least about 1.25-fold, at least about 1.5-fold, at least about 1.75-fold, at least about 2-fold, at least about 2.25-fold, at least about 2.5-fold, at least about 2.75-fold, at least about 3-fold, at least about 3.25-fold, at least about 3.5-fold, at least about 3.75-fold, at least about 4-fold, at least about 4.25-fold, at least about 4.5-fold, at least about 4.75-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, at least about 10-fold, at least about 11-fold, at least about 12-fold, and at least about 13-fold, at least about 14-fold, at least about 15-fold, at least about 16-fold, at least about 17-fold, at least about 18-fold, at least about 19-fold, at least about 20-fold, at least about 21-fold, at least about 22-fold, at least about 23-fold, at least about 24-fold, at least about 25-fold, at least about 26-fold, at least about 27-fold, at least about 28-fold, at least about 29-fold, at least about 30-fold, or higher. In addition, the apparent solubility, saturation solubility, and/or dissolution rate of the microparticulate drug composition may be increased by a factor that falls within a range of any two of the values listed above, such as (but not limited to), a range of from about 2-fold to about 5-fold, a range of from about 10-fold to about 25-fold, and the like.

In a particular (but non-limiting) embodiment, the microparticulate drug composition has an apparent solubility that is at least about 5-fold higher than that of an unprocessed form of the poorly soluble drug and at least about 2-fold higher than that of a microparticulate amorphous form of the poorly soluble drug.

Certain non-limiting embodiments of the present disclosure are also directed to a pharmaceutical composition comprising a dry powder aerosol formulation comprising any of the microparticulate drug compositions disclosed or otherwise contemplated herein.

Certain non-limiting embodiments of the present disclosure are also directed to a method of producing any of the microparticulate drug compositions or pharmaceutical compositions disclosed or otherwise contemplated herein. The method comprises at least the steps of: suspending NCs of a poorly soluble drug (as described herein above or otherwise contemplated herein) in a carrier solution to provide a nanocrystal/carrier suspension; and spray drying the nanocrystal/carrier suspension to form the inhalable microparticulate drug composition (as described herein above or otherwise contemplated herein). The carrier (also referred to herein as an excipient) may be, for example, a saccharide or saccharide derivative such as a highly soluble sugar as described elsewhere herein.

In a particular (but non-limiting) embodiment, the microparticulate drug compositions/pharmaceutical compositions of the present disclosure are produced using a bottom up method; thus, a micronization (milling) method is not used in their formation.

Certain non-limiting embodiments of the present disclosure are directed to a method that comprises administering to a subject in need thereof any of the pharmaceutical compositions disclosed or otherwise contemplated herein.

The pharmaceutical compositions may be administered via any mechanisms disclosed herein or otherwise contemplatable by a person having ordinary skill in the art. In one non-limiting embodiment, the administration occurs via an inhaler, which aerosolizes the NC-MPs.

The pharmaceutical compositions of the present disclosure may be administered for any purpose disclosed or otherwise contemplated herein, as well as for any purpose within the purview of a person having ordinary skill in the art. In one non-limiting embodiment, the pharmaceutical compositions are administered in a method of treating or reducing the occurrence of cancer. In another non-limiting embodiment, the pharmaceutical compositions are administered in a method of treating or reducing the occurrence of tuberculosis. However, these two treatment methods are not to be construed as limiting of the present disclosure, and any diseases, disorders, or conditions disclosed herein or otherwise contemplatable by a person having ordinary skill in the art (given the subject application) which may derive a therapeutic effect by treatment with the compositions disclosed herein also fall within the scope of the methods of the present disclosure.

The compositions and dosage forms of the present disclosure can be administered in a single dose treatment or in multiple dose treatments on a schedule and over a time period appropriate to the age, weight, and condition of the subject, the particular composition used, and the route of administration. In one non-limiting embodiment, a single dose of the composition according to the disclosure is administered. In other non-limiting embodiments, multiple doses are administered. The frequency of administration can vary depending on any of a variety of factors, e.g., severity of the symptoms, or whether the composition is used for prophylactic or curative purposes. For example, in certain non-limiting embodiments, the composition is administered once per month, twice per month, three times per month, every other week, once per week, twice per week, three times per week, four times per week, five times per week, six times per week, every other day, daily, twice a day, or three times a day. The duration of treatment (i.e., the period of time over which the composition is administered) can vary, depending on any of a variety of factors, e.g., subject response. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. Where used herein, unless otherwise indicated, the dosage amount refers to the amount of active pharmaceutical ingredient (API) that is administered to the subject.

The dosage of an administered active agent for humans will vary depending upon factors such as (but not limited to) the patient's age, weight, height, sex, general medical condition, and previous medical history. In certain non-limiting embodiments, where the active agent is administered by injection or infusion, the recipient may be provided with a dosage of the active agent that is in the range of from about 1 mg to about 1000 mg, and it may be administered as a single infusion or multiple injections, although a lower or higher dosage also may be administered. In certain non-limiting embodiments, the dosage may be in the range of from about 25 mg to about 100 mg of the active agent per square meter ($m^2$) of body surface area for a typical adult, although a lower or higher dosage also may be administered. Non-limiting examples of dosages of the active agent that may be administered to a human subject include, but are not limited to, those in ranges of 1 to 1000 mg, 1 to 600 mg, 1 to 500 mg, 1 to 400 mg, 1 to 300 mg, 1 to 200 mg, 100 to 600 mg, 100 to 500 mg, 100 to 400 mg, 100 to 300 mg, 100 to 200 mg, 150 to 600 mg, 150 to 500 mg, 150 to 400 mg, 150 to 300 mg, 150 to 250 mg, 150 to 200 mg, 200 to 7500 mg, 200 to 600 mg, 200 to 500 mg, 200 to 400 mg, 200 to 300 mg, and 200 to 250 mg, or any subrange within any of the aforementioned ranges. Dosages may be repeated as needed, for example (but not by way of limitation), once per week for 4-10 weeks, once per week for 8 weeks, or once per week for 4 weeks. It may also be given less frequently, such as (but not limited to) every other week for several months, or more frequently, such as twice weekly or by continuous infusion.

In certain non-limiting embodiments, the present disclosure is directed to a dosing regimen comprising multiple dosing cycles (e.g., wherein the first dosing cycle is a step-up, fractionated dosing cycle). In some non-limiting embodiments, the dose may range from 50 mg to 200 mg (e.g., from 50 mg to 175 mg, from 50 mg to 150 mg, from 50 mg to 125 mg, from 50 mg to 100 mg, from 50 mg to 75 mg, from 50 mg to 70 mg, from 52 mg to 100 mg, from 52 mg to 75 mg, from 50 mg to 180 mg, from 55 mg to 150 mg, from 55 mg to 100 mg, from 55 mg to 70 mg, from 55 mg to 65 mg, from 58 mg to 62 mg; e.g., about 60 mg, any subrange within any of the aforementioned ranges). In some non-limiting embodiments, the dose may be about 60 mg. In some non-limiting embodiments, the dose is about 1 mg. In some non-limiting embodiments, the dose is about 2 mg.

In some non-limiting embodiments, the dose is from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; about 20 mg, about 30 mg, about 45 mg, or e.g., about 60 mg, or any subrange within any of the aforementioned ranges). In some non-limiting embodiments, the dose is from about 12 mg to about 48 mg (e.g., from about 12 mg to about 42 mg, from about 12 mg to about 36 mg, from about 12 mg to about 30 mg, from about 18 mg to about 48 mg, from about 18 mg to about 42 mg, from about 24 mg to about 42 mg, from about 27 mg to about 42 mg, from about 24 mg to about 36 mg, from about 27 mg to about 33 mg, from about 28 mg to about 32 mg; e.g., about 24 mg, about 27 mg, about 30 mg, about 33 mg, or about 36 mg, or any subrange within any of the aforementioned ranges).

In some non-limiting embodiments, the dosing regimen comprises administration of a dose in a range of from 100 mg to 750 mg (e.g., from 100 mg to 725 mg, from 100 mg to 700 mg, from 100 mg to 675 mg, from 100 mg to 650 mg, from 100 mg to 625 mg, from 100 mg to 600 mg, from 100 mg to 575 mg, from 100 mg to 550 mg, from 100 mg to 525 mg, from 100 mg to 500 mg, from 100 mg to 475 mg, from 100 mg to 450 mg, from 100 mg to 425 mg, from 100 mg to 400 mg, from 100 mg to 375 mg, from 100 mg to 350 mg, from 100 mg to 325 mg, from 100 mg to 300 mg, from 100 mg to 275 mg, from 100 mg to 250 mg, or from 100 mg to 225 mg, from 100 mg to 200 mg, from 100 mg to 175 mg, from 100 mg to 150 mg, or from 100 mg to 125 mg, or any subrange within any of the aforementioned ranges).

In some non-limiting embodiments, the dosing regimen comprises administration of a dose in a range of from 200 mg to 750 mg (e.g., from 200 mg to 725 mg, from 200 mg to 700 mg, from 200 mg to 675 mg, from 200 mg to 650 mg, from 200 mg to 625 mg, from 200 mg to 600 mg, from 200 mg to 575 mg, from 200 mg to 550 mg, from 200 mg to 525 mg, from 200 mg to 500 mg, from 200 mg to 475 mg, from 200 mg to 450 mg, from 200 mg to 425 mg, from 200 mg to 400 mg, from 200 mg to 375 mg, from 200 mg to 350 mg, from 200 mg to 325 mg, from 200 mg to 300 mg, from 200 mg to 275 mg, from 200 mg to 250 mg, or from 200 mg to 225 mg, or any subrange within any of the aforementioned ranges).

In some non-limiting embodiments, the dosing regimen comprises administration of a dose in a range of from 300 mg to 750 mg (e.g., from 300 mg to 725 mg, from 300 mg to 700 mg, from 300 mg to 675 mg, from 300 mg to 650 mg, from 300 mg to 625 mg, from 300 mg to 600 mg, from 300 mg to 575 mg, from 300 mg to 550 mg, from 300 mg to 525 mg, from 300 mg to 500 mg, from 300 mg to 475 mg, from 300 mg to 450 mg, from 300 mg to 425 mg, from 300 mg to 400 mg, from 300 mg to 375 mg, from 300 mg to 350 mg, or from 300 mg to 325 mg, or any subrange within any of the aforementioned ranges).

In some non-limiting embodiments, the dosing regimen comprises administration of a dose in a range of from 400 mg to 750 mg (e.g., from 400 mg to 725 mg, from 400 mg to 700 mg, from 400 mg to 675 mg, from 400 mg to 650 mg, from 400 mg to 625 mg, from 400 mg to 600 mg, from 400 mg to 575 mg, from 400 mg to 550 mg, from 400 mg to 525 mg, from 400 mg to 500 mg, from 400 mg to 475 mg, from 400 mg to 450 mg, or from 400 mg to 425 mg, or any subrange within any of the aforementioned ranges).

In some non-limiting embodiments, the dosing regimen comprises administration of a dose in a range of from 500 mg to 750 mg (e.g., from 500 mg to 725 mg, from 500 mg to 700 mg, from 500 mg to 675 mg, from 500 mg to 650 mg, from 500 mg to 625 mg, from 500 mg to 600 mg, from 500 mg to 575 mg, from 500 mg to 550 mg, or from 500 mg to 525 mg, or any subrange within any of the aforementioned ranges).

In some non-limiting embodiments, the dosing regimen comprises administration of a dose in a range of from 600 mg to 750 mg (e.g., from 600 mg to 725 mg, from 600 mg to 700 mg, from 600 mg to 675 mg, from 600 mg to 650 mg, from 600 mg to 625 mg, or any subrange within any of the aforementioned ranges).

In some non-limiting embodiments, the active agent is provided in a concentration of about 1 nM, about 5 nM, about 10 nM, about 25 nM, about 50 nM, about 75 nM, about 100 nM, about 150 nM, about 200 nM, about 250 nM, about 300 nM, about 350 nM, about 400 nM, about 500 nM, about 550 nM, about 600 nM, about 700 nM, about 800 nM, about 900 nM, about 1 μM, about 2 μM, about 3 μM, about 4 μM, about 5 μM, about 6 μM, about 7 μM, about 8 μM, about 9 μM, about 10 μM, about 15 μM, about 20 μM, about 25 μM, about 30 μM, about 35 μM, about 40 μM, about 45 μM, about 50 μM, about 60 μM, about 70 μM, about 75 μM, about 80 μM, about 90 μM, about 100 μM, about 125 μM, about 150 μM, about 175 μM, about 200 μM, about 250 μM, about 300 μM, about 350 μM, about 400 μM, about 500 μM, about 600 μM, about 700 μM, about 750 μM, about 800 μM, about 900 μM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 400 mM, about 500 mM, about 600 mM, about 700 mM, about 800 mM, about 900 mM, about 1000 mM, about 1 M, about 1.1 M, about 1.2 M, about 1.3 M, about 1.4 M, about 1.5 M, about 1.6 M, about 1.7 M, about 1.8 M, about 1.9 M, about 2 M, about 3 M, about 4 M, about 5 M, about 6 M, about 7 M, about 8 M, about 9 M, about 10 M, about 15 M, about 20 M, about 25 M, about 30 M, about 35 M, about 40 M, about 45 M, about 50 M, about 75 M, about 100 M, or any range in between any two of the aforementioned concentrations, including said two concentrations as endpoints of the range, or any number in between any two of the aforementioned concentrations.

When administered orally, the active agent composition may be protected from digestion. This can be accomplished either by complexing the NC-MPs with a composition to render it resistant to acidic and enzymatic hydrolysis or by packaging the NC-MPs in an appropriately resistant carrier such as (but not limited to) a liposome, e.g., such as shown in U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. For topical transdermal administration, the agents are formulated into ointments, creams, salves, powders, and gels. Transdermal delivery systems can also include (for example but not by way of limitation) patches. The present compositions can also be administered in sustained delivery or sustained release mechanisms. For example, biodegradeable microspheres or capsules or other biodegradeable polymer configurations capable of sustained delivery can be included herein.

The compositions of the present disclosure may be formulated as implants, in the form of either biodegradable microparticles or small squared films comprising the microparticles of the present disclosure. The following describes methods of making such implants. Microparticles (e.g., 5-100 micrometers) containing different loadings of the compounds of the present disclosure, such as heteroarotinoids, are prepared by spray drying suspensions of the nanocrystals of the compounds and a biodegradable polymer (for example, polylactic acid of molecular weights 50,000-100,000) or polylactic-co-glycolic acid copolymer (e.g., proportions 75:25 or 50:50). Microparticles may contain, e.g., 10-50% wt/wt drug:polymer and can be implanted alone, or in a biodegradable film, e.g., as an implantable chitosan-egg phosphatidylcholine (ePC) films. To make such chitosan-egg phosphatidylcholine (ePC) films, chitosan flakes and ePC can be dissolved in a 1% acetic acid at a ratio of 1:0.8 (wt/wt). Microparticles containing the drug in nanocrystal form are dispersed in the chitosan-ePC solution in different proportions (e.g., 1:3, 1:5, 1:7 and 1:10 wt/wt) to achieve the release of different drug doses. The resulting microparticle-chitosan-ePC suspension can be poured into a Teflon dish to have a 2-3 mm thickness and allowed to dry in a covered dessicator for 5 days. After the films are dry, they can be cut into small squares of 15×15 $mm^2$. The implants can be made in different forms, including but not limited to thin films, rods, and wafers. Other biodegradable polymers that can be used to make implants include, but are not limited to, poly-lactic acid, poly-lactic-co-glycolic acid copolymer, poly-caprolactone, poly-sebacic acid, poly-adipic acid, poly (3-hydroxybutyric acid), poly(3-hydroxybutyrate-co-3-hydroxyvalerate, poly-trimethylene carbonate, chitosan, chitin, gelatin, collagen, and hyaluronic acid.

In non-limiting embodiments, gels comprising the NC-MPs of the present disclosure can be made by combining the NC-MPs in various proportions to a sodium alginate gel base or carbomer jelly base to form a homogeneous gel suitable for topical application.

In non-limiting embodiments, ointments comprising the NC-MPs of the present disclosure can be made by combining the NC-MPs in various proportions to a Hydrophilic Petrolatum USP base, Lanolin, USP base or to Polyethylene glycol ointment, NF to form a homogeneous ointment suitable for topical application.

In non-limiting embodiments, creams comprising the NC-MPs of the present disclosure can be made by combining the NC-MPs in various proportions in suspension in water and glycerin (e.g., 20:1 parts) and emulsified in a mixture of e.g., Lanolin, Beeswax USP-NF and Cetyl alcohol, plus a Tween 80 and Span 80.

Several gel, ointment, and/or cream compositions that can be used are shown in Garcia-Contreras L, Abu-Izza K, Lu DR. "Biodegradable cisplatin microspheres for direct brain injection: Preparation and characterization." *Pharm Dev Technol* (1997) 2(1): 53-65.

For inhalation, the present compositions can be delivered using any system known in the art, including (but not limited to) dry powder aerosols, liquids delivery systems, air jet nebulizers, propellant systems, and the like. For example (but not by way of limitation), the pharmaceutical formulation can be administered in the form of an aerosol or mist. For aerosol administration, the formulation can be supplied in finely divided form along with a surfactant and propellant. In another non-limiting aspect, the device for delivering the formulation to respiratory tissue is an inhaler in which the formulation vaporizes. Other liquid delivery systems include (for example but not by way of limitation) air jet nebulizers.

In one non-limiting aspect, the active agent is incorporated in lipid monolayers or bilayers, such as (but not limited to) liposomes. Liposomes and liposomal formulations can be prepared according to standard methods and are also well known in the art, such as (but not limited to) those disclosed in U.S. Pat. Nos. 6,110,490; 6,096,716; 5,283,185; 5,279,833; 4,235,871; 4,501,728; and 4,837,028.

In one non-limiting aspect, the compositions are prepared with carriers that will protect the active agent against rapid elimination from the body, such as (but not limited to) a controlled release formulation, including implants and microencapsulated delivery systems. Biodegradable, biocompatible polymers can be used, such as (but not limited to) ethylene vinyl acetate, polyanhydrides, polyglycolic acid, collagen, polyorthoesters, and polylactic acid. Methods for preparation of such formulations will be apparent to those skilled in the art.

The active agents in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active agent is combined in a mixture with one or more pharmaceutically suitable excipients. Sterile phosphate-buffered saline is one non-limiting example of a pharmaceutically suitable excipient.

The acid addition salts may include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, cam phorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N?-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methyl sulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Non-limiting examples of routes of administration of the compositions described herein include parenteral injection, e.g., by subcutaneous, intramuscular, or transdermal delivery. Other forms of injection include (but are not limited to) intravenous, intraarterial, intralymphatic, intrathecal, intraocular, intranasal, intracranial, intracerebral, intraperitoneal, or intracavitary injection. In parenteral administration, the compositions will be formulated in a unit dosage injectable form such as (but not limited to) a solution, suspension, or emulsion, in association with a pharmaceutically acceptable excipient. Such excipients are inherently nontoxic and nontherapeutic. Non-limiting examples of such excipients include saline, Ringer's solution, dextrose solution, and Hanks' solution. Nonaqueous excipients such as (but not limited to) fixed oils and ethyl oleate may also be used. An alternative non-limiting excipient is 5% dextrose in saline. The excipient may contain minor amounts of additives such as (but not limited to) substances that enhance isotonicity and chemical stability, including buffers and preservatives. The active agents can be delivered or administered alone or as pharmaceutical compositions by any means known in the art, such as (but not limited to) systemically, regionally, or locally, for example by intraarterial, intrathecal (IT), intravenous (IV), parenteral, intrapleural cavity, topical, oral, or local administration, as subcutaneous, intratracheal (e.g., by aerosol) or transmucosal administration (e.g., buccal, bladder, vaginal, uterine, rectal, and/or nasal mucosa). Administration can also be localized directly into a tumor. Administration into the systemic circulation by intravenous, inhalation, mucosal, or subcutaneous administration is typical. Intravenous administration can be, for example (but not by way of limitation), by infusion over a period such as (but not limited to) 30-90 min or by a single bolus injection, or by other regimens as described elsewhere herein.

Formulated compositions comprising the active agents of the present disclosure can be provided in unit dosage form, e.g., in ampoules or in multi-dose containers, with an added preservative. Compositions can also take such forms as suspensions, solutions, or emulsions in oily or aqueous vehicles, and can contain formulatory agents such as suspending, stabilizing, and/or dispersing agents.

In some non-limiting methods, the patient is administered the active agent every one, two, three, or four weeks, for example. The dosage depends on the frequency of administration, condition of the patient, response to prior treatment (if any), whether the treatment is prophylactic or therapeutic, and whether the disorder is acute or chronic, among other factors.

The number of dosages administered may depends on the severity and temporal nature of the disorder (e.g., whether presenting acute or chronic symptoms) and the response of the disorder to the treatment. For acute disorders or acute exacerbations of a chronic disorder, between 1 and 10 doses may be used. Sometimes a single bolus dose, optionally in divided form, is sufficient for an acute disorder or acute exacerbation of a chronic disorder. Treatment can be repeated for recurrence of an acute disorder or acute exacerbation. For chronic disorders, the active agent may be administered at regular intervals, such as (but not limited to) weekly, fortnightly, monthly, quarterly, every six months for at least 1, 5, or 10 years, or for the life of the patient.

Compositions can be administered in a single dose treatment or in multiple dose treatments on a schedule and over a time period appropriate to the age, weight, and condition of the subject, the particular composition used, and the route of administration. In one non-limiting embodiment, a single dose of the composition according to the disclosure is administered. In other non-limiting embodiments, multiple doses are administered. The frequency of administration can vary depending on any of a variety of factors, e.g., severity of the symptoms, degree of immunoprotection desired, or whether the composition is used for prophylactic or curative purposes. For example, in certain non-limiting embodiments, the composition is administered once per month, twice per month, three times per month, every other week, once per week, twice per week, three times per week, four times per week, five times per week, six times per week, every other day, daily, twice a day, or three times a day. The duration of treatment (i.e., the period of time over which the composition is administered) can vary, depending on any of a variety of factors, e.g., subject response. For example (but not by way of limitation), the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The dosage of an administered active agent for humans will vary depending upon factors such as (but not limited to) the patient's age, weight, height, sex, general medical condition, and previous medical history. A dosage may be provided as several smaller amounts. For example, a single dosage of 500 mg may be administered as ten 50 mg tablets or capsules, or as five 100 mg tablets or capsules. The amounts of doses or dosages described herein may be provided in a single capsule, tablet, injection, infusion, or other more of delivery. Or, the amounts of drug which comprise the doses or dosages described herein may be provided in two or more (e.g., 2, 3, 4, 5, 6, 7, 8, 9, 10, 11, or 12) capsules, tablets, injections, infusions, or other modes of delivery.

In certain non-limiting embodiments, the recipient may be provided with a dosage of the active agent that is in the range of from about 1 mg to about 1000 mg. A lower or higher dosage also may be administered. In certain non-limiting embodiments, the dosage may be in the range of from about 25 mg to about 100 mg of the active agent per square meter ($m^2$) of body surface area for a typical adult, although a lower or higher dosage also may be administered. Non-limiting examples of dosages of the active agent that may be administered to a human subject further include 1 to 750 mg, 1 to 600 mg, 1 to 500 mg, 1 to 400 mg, 1 to 300 mg, 1 to 200 mg, or 1 to 100 mg, although higher or lower doses may be used. Dosages may be repeated as needed, for example (but not by way of limitation), once per week for 4-10 weeks, once per week for 8 weeks, or once per week for 4 weeks. In certain non-limiting embodiments, the dosage can be provided as an infusion, for example as a single injection or as multiple injections. It may also be given less frequently, such as (but not limited to) every other week for several months, or more frequently, such as twice weekly, or by continuous infusion.

In some non-limiting embodiments, a per capsule or tablet dose may range from 25 mg to 200 mg (e.g., from 25 mg to 175 mg, from 25 mg to 150 mg, from 25 mg to 125 mg, from 25 mg to 100 mg, from 25 mg to 75 mg, from 25 mg to 70 mg, from 40 mg to 100 mg, from 40 mg to 75 mg, from 40 mg to 175 mg, from 40 mg to 150 mg, from 40 mg to 125 mg, from 40 mg to 70 mg, from 40 mg to 60 mg, or from 45 mg to 55 mg). In some non-limiting embodiments, the dose per capsule or tablet may be about 50 mg.

In some non-limiting embodiments, the dose per capsule or tablet is from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; about 20 mg, about 30 mg, about 45 mg, or e.g., about 60 mg). In some non-limiting embodiments, the dose is from about 12 mg to about 48 mg (e.g., from about 12 mg to about 42 mg, from about 12 mg to about 36 mg, from about 12 mg to about 30 mg, from about 18 mg to about 48 mg, from about 18 mg to about 42 mg, from about 24 mg to about 42 mg, from about 27 mg to about 42 mg, from about 24 mg to about 36 mg, from about 27 mg to about 33 mg, from about 28 mg to about 32 mg; e.g., about 24 mg, about 27 mg, about 30 mg, about 33 mg, or about 36 mg).

In some non-limiting embodiments, the dosing regimen comprises administration of a loading dose, such as from 20 mg to 200 mg (e.g., from 20 mg to 175 mg, from 20 mg to 150 mg, from 20 mg to 100 mg, from 20 mg to 75 mg, from 30 mg to 175 mg, from 40 mg to 175 mg, from 45 mg to 175 mg, from 50 mg to 175 mg, from 30 mg to 150 mg, from 40 mg to 100 mg, from 45 mg to 75 mg, from 50 mg to 70 mg, from 55 mg to 65 mg, from 58 mg to 62 mg; e.g., about 60 mg). In some non-limiting embodiments, the dose is from about 12 mg to about 48 mg (e.g., from about 12 mg to about 42 mg, from about 12 mg to about 36 mg, from about 12 mg to about 30 mg, from about 18 mg to about 48 mg, from about 18 mg to about 42 mg, from about 24 mg to about 42 mg, from about 27 mg to about 42 mg, from about 24 mg to about 36 mg, from about 27 mg to about 33 mg, from about 28 mg to about 32 mg; e.g., about 24 mg, about 27 mg, about 30 mg, about 33 mg, or about 36 mg).

In certain non-limiting embodiments, the per day dosage for administration to a subject is in a range of 1 mg/kg to 25 mg/kg, or 2 mg/kg to 24 mg/kg, or 3 mg/kg to 22 mg/kg, or 4 mg/kg to 20 mg/kg, or 5 mg/kg to 17.5 mg/kg, or 5 mg/kg to 15 mg/kg, or 5 mg/kg to 12.5 mg/kg, or 6 mg/kg to 25 mg/kg, or 6 mg/kg to 20 mg/kg, or 6 mg/kg to 15 mg/kg, or 6 mg/kg to 12 mg/kg.

In certain non-limiting embodiments, the amount of the active agent delivered to the subject per dose is in a range of about 100 mg to about 1000 mg, or about 200 mg to about 1000 mg, or about 300 mg to about 1000 mg, or about 400 mg to about 1000 mg, or about 250 mg to about 900 mg, or about 400 mg to about 900 mg, or about 400 mg to about 850 mg, or about 400 mg to about 800 mg, or about 400 mg to about 700 mg, or about 420 mg to about 840 mg, or about 500 mg to about 650 mg, or about 500 mg to about 1000 mg, or about 500 mg to about 900 mg, or about 500 mg to about 850 mg, or about 500 mg to about 800 mg, or about 500 mg to about 700 mg. The total dose to be delivered can be provided in a single capsule, tablet, injection, or bolus (or other dosage form), or in multiple capsules, tablets, injections, or boluses (or other dosage forms).

In at least certain non-limiting embodiments, when the active agent is provided in the form of a capsule or tablet, the capsule or tablet should disintegrate within about 5-10 minutes, and in the gastrointestinal (GI) tract the active agent should dissolve in about 30 minutes.

In at least certain non-limiting embodiments, once the active agent is absorbed from the GI tract, it should produce a (therapeutic) concentration of at least 1.7 μg/ml, or at least 4 mM, in the target tissue. In at least certain non-limiting embodiments, the dosage form is designed to provide a therapeutic concentration of the active agent in the subject for at least about 12 to 24 hours, when the active agent is administered once a day.

The NCs presently disclosed have enhanced shelf-life stability. Nanocrystals prepared by the top-down method are likely to have amorphous parts, resulting from the heat produced while micronizing or milling the material, or exhibit stronger particulate interforces as a result of the charges produced by the micronization or milling. Therefore, they require specialized ingredients to be stabilized. In contrast, the NCs produced with the methods of the present disclosure are 100% crystalline and have a longer shelf life and do not require special excipients to preserve the stability of the drug in the nanocrystal.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. For topical transdermal administration, the agents are formulated into ointments, creams, salves, powders, and gels. Transdermal delivery systems can also include (for example, but not by way of limitation) patches. The present compositions can also be administered in sustained delivery or sustained release mechanisms. For example, biodegradeable microspheres or capsules or other biodegradeable polymer configurations capable of sustained delivery of a peptide can be included herein.

For inhalation, the present compositions can be delivered using any system known in the art, including (but not limited to) dry powder aerosols, liquids delivery systems, air jet nebulizers, propellant systems, and the like. For example (but not by way of limitation), the pharmaceutical formulation can be administered in the form of an aerosol or mist. For aerosol administration, the formulation can be supplied in finely divided form along with a surfactant and propellant. In another non-limiting aspect, the device for delivering the formulation to respiratory tissue is an inhaler in which the formulation vaporizes. Other liquid delivery systems include (for example, but not by way of limitation) air jet nebulizers.

In at least one non-limiting embodiment, the heteroarotinoid concentrations in the cervix, uterus, fallopian tubes, and ovaries are maintained above the theoretical therapeutic level for at least 72 hours (3 days) after a single administration of a vaginal suppository.

Examples of vaginal suppository compositions that may be used as carriers of the active agents (NC-MPs) of the present disclosure include, but are not limited to, those shown in Mahjabeen, S., Chandra, V., Hatipoglu, S. M., Benbrook, D. M. and Garcia-Contreras, L. "Optimization of a Vaginal Suppository Formulation to Deliver SHetA2 as a Novel Treatment for Cervical Dysplasia," Journal of Pharmaceutical Sciences. 2018; 107(2): 638-646; Mahjabeen, S., Hatipoglu, S. M., Benbrook, D. M., Kosanke, S. D., Garcia-Contreras, D., Garcia-Contreras, L. "Influence of the estrus cycle of the mouse on the disposition of SHetA2 after vaginal administration," European Journal of Pharmaceutics and Biopharmaceutics. 2018; 130: 272-280; Mahjabeen, S., Hatipoglu, S. M., Benbrook, D. M., Garcia-Contreras, L. "Pharmacokinetics and Pharmacodynamics of Escalating Doses of SHetA2 after Vaginal Administration to Mice," Journal of Pharmaceutical Sciences. 2018; 107: 3179-3186; and Mahjabeen, S., Hatipoglu, S. M., Kosanke, S. D., Garcia-Contreras, D., Benbrook, D. M., Garcia-Contreras, L. "Vaginal suppositories containing SHetA2 to treat cervical dysplasia: pharmacokinetics of daily doses and preliminary safety profile," Journal of Pharmaceutical Sciences. 2020. 109 (6): 2000-2008.

Formation of Larger NC-MPs

In certain non-limiting embodiments of the present disclosure, the NC-MPs can be formed to have diameters of up to, for example, 500 μm. For example, NC-MPs of up to 50 μm can be prepared by spray drying using a suspension of the NCs in an aqueous solution of a highly-soluble sugar carrier as described elsewhere herein (such as sucrose, trehalose, maltose, mannitol, sorbitol, and lactose). NC-MPs of up to 500 μm can be prepared by pelletizing processes, or other controlled processes of agglomeration, including refined methods of wet granulation. Dry granulation or direct compression processes using suitable excipients (e.g., Avicel, microcrystalline cellulose) can be used for the manufacture of NC-MPs having diameters in a range of 50-500 μm. The NC formulations of heteroarotinoids, provided as a suspension, can be used in a wet granulation process with traditional excipients (e.g., lactose, microcrystalline cellulose, Carboxymethylcellulose, methyl cellulose, polyvinyl pyrrolidone, croscarmellose, and starches) to produce tablets. Tablet formulations for drugs that are poorly soluble in water have heretofore required a complex combination of excipients and especialized processes (such as Hot Melt Extrusion, HME), which increases the cost of producing these tablets. The methods of the present disclosure, which use NC formulations of heteroarotinoids, enable the use of traditional excipients and methods of tablet production, which will simplify the process to manufacture and decrease production costs.

As previously noted, SHetA2 is provided only as one non-limiting example of a poorly water soluble drug that may be utilized in accordance with the present disclosure. The active agent of the microparticulate drug compositions (NC-MPs) of the present disclosure is not intended to be limited to SHetA2; rather, the scope of the present disclosure includes the use of any poorly soluble drug as defined or described herein. In particular, other heteroarotinoids that may be used as the active agent include (but are not limited to) any heteroarotinoid disclosed in U.S. Pat. No. 6,586,460 (see, for example, Columns 2-5 thereof) and U.S. Pat. No. 7,612,107 (see, for example, Columns 7-9 thereof); non-limiting examples thereof include SHetA2, SHetA3, SHetA4, SHetC2, SHetD3, SHetD4, SHetD5, SHet50, SHet65, SHet100, OHet72, NHet17, NHet86, NHet90, and others shown for example in Tables 1-9. Also as previously noted, other poorly soluble active agents that may be used in the presently disclosed formulations include, but are not limited to, CDK4/6 inhibitors such as, but not limited to Palbociclib, Abemaciclib, Ribociclib, and ON123300; PARP inhibitors such as, but not limited to Olaparib, Niraparib, Rucaparib, Talazoparib, Veliparib, Pamiparib, CEP 9722, and E7016; Azabicyclooctan-3-one derivatives such as PRIMA-1; and PRIMA-$1^{MET}$ (APR246); and anti-tubercular riminophenazine analogs, such as, for example, TBI-161, TBI-166, TBI-416, TBI-443, TBI-444, TBI-449, TBI-450, TBI-678, TBI-688, TBI-1002, TBI-1004, TBI-1010, and clofazimine.

In certain non-limiting embodiments, active agents of the present disclosure of different classes can be administered in combination. For example, a heteroarotinoid can be administered in combination with a CDK4/6 inhibitor, a PARP inhibitor, an Azabicyclooctan-3-one derivative, and/or a riminophenazine analog. A CDK4/6 inhibitor can be administered in combination with a PARP inhibitor, an Azabicyclooctan-3-one derivative, and/or a riminophenazine analog. A PARP inhibitor can be administered in combination with an Azabicyclooctan-3-one derivative, and/or a riminophenazine analog. An Azabicyclooctan-3-one derivative can be administered in combination with a riminophenazine analog. The active agents may be administered together, or in sequence.

EXAMPLES

The novel embodiments of the present disclosure, having now been generally described, will be more readily understood by reference to the following examples and embodiments, which are included merely for purposes of illustration of certain aspects and embodiments of the present disclosure, and are not intended to be limiting. The following detailed examples and embodiments are to be construed, as noted above, only as illustrative, and not as limitations of the present disclosure in any way whatsoever. Those skilled in the art will promptly recognize appropriate variations from the various compositions, structures, components, procedures, and methods.

In a particular (but non-limiting) embodiment, the microparticulate drug compositions or pharmaceutical compositions disclosed or otherwise contemplated herein comprise SHetA2, which induces apoptosis in cancer cells without harming normal cells.

Formation of SHetA2 Nanocrystals and Use in Production of Inhalable SHetA2 Microparticles Methods and Results:

Chemicals

Dichloromethane (DCM) (Sigma, St. Louis, MO, USA), methanol (HPLC grade ≥99.9%, Sigma, St. Louis, MO, USA), sodium acetate trihydrate (Reagent plus ≥99.0%, Sigma, St. Louis, MO, USA), mannitol (≥98.0%, Sigma, St. Louis, MO, USA), poly(vinyl alcohol) (PVA, $M_w$: 25000 Polysciences, Warrington, PA, USA) and SHetA2.

Instruments

In this work, a sonic dismembrator (Fisher Scientific, Pittsburgh, PA, USA) and an ultrasonic bath (Branson, Loveland, CO, USA) were used to fabricate the drug nanocrystals (NCs). Buchi Mini Spray Dryer B-290 (New Castle, DE, USA) was used to manufacture the microparticles (MPs). The geometric diameter ($d_g$) of NCs and NC-MPs were measured directly from the images obtained with a scanning electron microscope (SEM) (JEOL JSM-880, JEOL USA, Inc., Peabody, MA) with the aid of ImageJ 1.49n software (NIH, USA). The morphology of the MPs was evaluated by SEM. The volume diameter ($d_v$) of NCs and MPs was measured by laser diffraction using a HELOS system with RODOS dry dispersing unit (Sympatec Inc., Lawrenceville, NJ). The production and analysis of the products and compositions of the present disclosure are not limited to the use of these particular instruments. Any other instruments capable of functioning in a similar manner could be used in lieu of those described herein.

In Vivo

Friend Leukemia Virus B (FVB) male mice and Male Dunkin Hartley guinea pigs were used in in vivo experiments.

Fabrication of SHetA2 Nanocrystals

SHetA2 NCs were prepared using a bottom up approach. In one non-limiting embodiment, the process was formulated to yield NCs with the smallest possible geometric diameter ($d_g$) using Design of Experiments (DoE) software. Briefly, 75 mg of SHetA2 was dissolved in 1 mL of DCM. A round bottom flask containing 10 mL of 1% (w/v) PVA was placed in an ultrasonic bath. The SHetA2-DCM solution was injected into the PVA solution while operating simultaneously the sonic dismembrator and ultrasonic bath, each at different settings described below. The resulting NCs were then separated by centrifugation at 5500 rpm for 30 min. The pellet containing the NCs was washed with deionized water at least 3 times to remove residual PVA. The NCs in the washed pellet were then reconstituted in deionized water and stored at −80° C. The formulation and fabrication process was calculated to yield NCs with the smallest possible geometric diameter ($d_g$) using $2^4$ factorial design software (DESIGN-EXPERT® software; DoE, Minneapolis, MN)). The parameters entered in the DoE were drug concentration in the organic phase (30-75 mg/ml), sonication power (10-24 Watts), sonication time (30-60 minutes), and an ultrasonication time of 20-40 minutes, as shown in Table 10 below.

The value of $d_g$ calculated herein is an average of measurements of at least 200 individual NCs from each batch. The geometric standard deviation (GSD) of $d_g$ was calculated using Equation I:

$$GSD = [D_{84\%} / D_{16\%}]^{1/2} \quad \text{(Eqn. I)}$$

where $D_{84\%}$ and $D_{16\%}$ represent the diameters at the cumulative percentile of 84% and 16% of the particle size distribution after it has been "normalized."

TABLE 10

Experimental Parameters and Sizes and Size Distributions of SHetA2 NCs

| Exp. # | Sonication Power (W) | Sonication Time (min) | Drug conc. (mg/mL) | Ultrasonication Time (min) | $d_g$ (μm) | GSD | Span |
|---|---|---|---|---|---|---|---|
| 1 | 10 | 30 | 30 | 20 | 0.396 | 1.85 | 0.0-1.40 |
| 2 | 24 | 30 | 30 | 20 | 0.573 | 1.87 | 0.0-1.00 |
| 3 | 10 | 60 | 30 | 20 | 0.388 | 1.75 | 0.0-0.80 |
| 4 | 24 | 60 | 30 | 20 | 0.380 | 1.69 | 0.0-0.80 |
| 5 | 10 | 30 | 30 | 40 | 0.372 | 1.76 | 0.0-0.70 |
| 6 | 24 | 30 | 30 | 40 | 0.343 | 1.57 | 0.0-0.60 |
| 7 | 10 | 60 | 30 | 40 | 0.357 | 1.71 | 0.0-0.80 |
| 8 | 24 | 60 | 30 | 40 | 0.421 | 1.71 | 0.0-1.00 |
| 9 | 10 | 30 | 75 | 20 | 0.710 | 1.58 | 0.0-0.70 |
| 10 | 24 | 30 | 75 | 20 | 0.690 | 1.70 | 0.0-0.35 |
| 11 | 10 | 60 | 75 | 20 | 0.157 | 2.00 | 0.0-1.00 |
| 12 | 24 | 60 | 75 | 20 | 0.635 | 1.60 | 0.0-1.30 |
| 13 | 10 | 30 | 75 | 40 | 0.602 | 1.58 | 0.0-0.80 |
| 14 | 24 | 30 | 75 | 40 | 0.477 | 1.63 | 0.0-1.00 |
| 15 | 10 | 60 | 75 | 40 | 0.439 | 1.61 | 0.0-1.20 |
| 16 | 24 | 60 | 75 | 40 | 0.557 | 1.54 | 0.0-1.40 |

Spray Drying of SHetA2 NCs into MPs (SHetA2 NC-MPs)

The aerodynamic diameter ($d_a$) is the best parameter to use to predict how a particle or droplet will behave in an air stream. The $d_a$ is defined as the diameter of a unit density sphere that has the same terminal setting velocity in air as the actual particle and is described by Equation II:

$$V_{TS} = r_0 D_a^2 g / 18h = r_p D_v^2 g / 18hc \quad \text{(Eqn. II)}$$

where $V_{TS}$ is the terminal settling velocity of the unit density sphere; $r_0$ is the unit density; g is the acceleration of gravity; h is the air viscosity; $r_p$ is the particle density; $D_v$ is the equivalent volume diameter; and c is the shape factor of the particle. This equation has important implications for the production of dry powder aerosols, as it implies that the terminal settling velocity of particles increases proportionately with their size. Thus, under the principles of lung deposition, large particles would be more likely to deposit by inertial impaction in the upper respiratory tract, where air velocity is high and the air flow is turbulent, whereas smaller particles would deposit by sedimentation in the terminal bronchioles and alveolar regions.

NCs from the batch of SHetA2 NCs with the smallest $d_g$ (experiment #11 from Table 10) were suspended with mannitol in water for formulation by spray-drying into inhalable nanocrystal microparticles (NC-MPs). The MP size ($d_g$ and $d_v$) and distribution GSD were optimized by entering the following formulation composition and manufacturing parameters into a second DoE: feed concentration (0.5% to 1.5% of NCs), spray drying temperature (120° C. to 150° C.), and mannitol ratio (10% to 50%). For example, the feed concentration represents the grams (g) of total solids (NCs and mannitol) suspended in milliliters (mL) of deionized water. Thus, a feed concentration of 0.5% represents 0.005 g of total solids per 1.0 mL of water. In one example, 50 mg of total solids suspended in 1 mL of deionized water results in a 0.5% feed concentration. An "X %" mannitol ratio indicates that X % of the total solids was mannitol, and (100−X) % of the total solids was NCs. For example, the feed concentration for #8 in Table 2 is 0.5%, which means 50 mg of total solids (NCs and mannitol) was suspended in 10 mL of deionized water. The mannitol ratio was 50%, indicating that 50% of the total solids was mannitol, and 50% of the total solids was NCs. Thus, in the case of experiment #8 in Table 2, 25 mg of NCs and 25 mg of mannitol were suspended in 10 mL of water, providing a 0.5% feed concentration and a 50% mannitol ratio. SEM images of SHetA2 NCs and NC-MPs are shown in Panels (a) and (b) of FIG. 1, respectively. Composition results are shown in Table 11.

TABLE 11

Spray Drying Parameters and Sizes and Size Distributions of SHetA2 NC-MPs

| Exp. # | Feed Conc. % | Mannitol Ratio % | Temperature (° C.) | $d_v$ | GDS ($d_v$) | $d_g$ | GSD ($d_g$) | Yield % |
|---|---|---|---|---|---|---|---|---|
| 1 | 1.5 | 10 | 150 | 3.45 | 1.68 | 1.87 | 1.32 | 37.80 |
| 2 | 0.5 | 10 | 120 | 2.99 | 1.60 | 2.62 | 1.22 | 20.72 |
| 3 | 0.5 | 10 | 150 | 3.04 | 1.62 | 2.60 | 1.33 | 17.52 |
| 4 | 1.5 | 50 | 120 | 2.62 | 1.68 | 1.81 | 1.35 | 36.81 |
| 5 | 1.5 | 10 | 120 | 3.08 | 1.59 | 2.57 | 1.28 | 14.94 |
| 6 | 1.5 | 50 | 150 | 2.69 | 3.30 | 2.22 | 1.33 | 35.00 |
| 7 | 0.5 | 50 | 150 | 2.41 | 1.70 | 1.53 | 1.19 | 20.90 |
| 8 | 0.5 | 50 | 120 | 2.53 | 1.70 | 2.30 | 1.36 | 35.00 |

Particle Size Distribution of NCs and NC-MPs

The value of $d_g$ is an average of measurements of at least 200 individual NCs from each batch. The morphology of the MPs was evaluated by SEM. The value of $d_v$ is an average of measurements of at least 200 individual MPs from each batch. Measurements were performed in triplicate at a dispersion pressure of 0.5 bars. The geometric standard deviation (GSD) of both $d_g$ and $d_v$ was calculated using Equation I.

Figure 2:
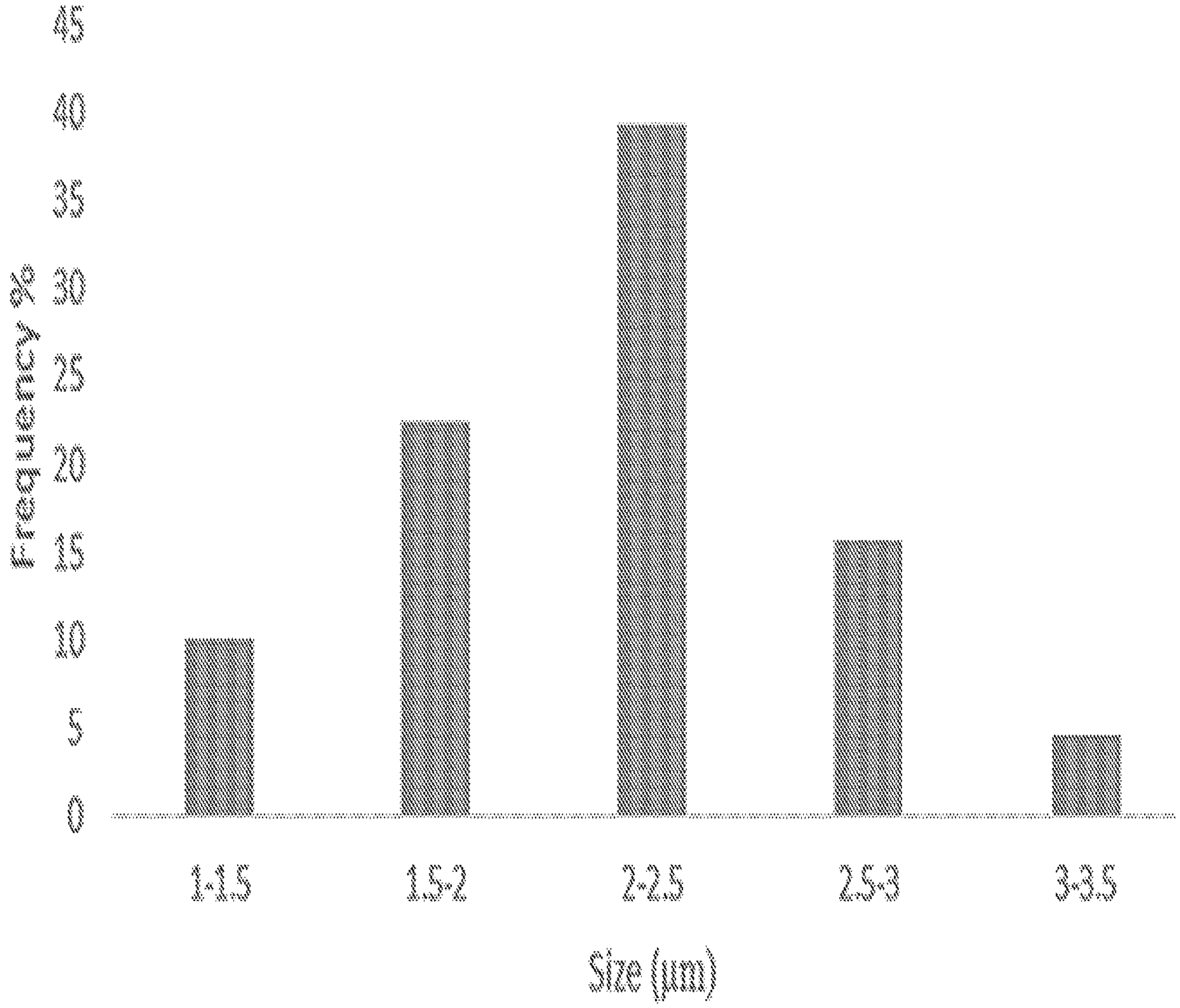
FIG. 2 shows the size distribution of the respirable fraction of microparticles formed by SHetA2 NCs formulated into microparticles (NC-MPs). The sum of all bars adds to 95%.

The size of NC-MPs produced ranged from $d_v$=3.45 μm and GSD=3.30 to $d_v$=2.41 μm and GSD=1.59. The MPs of experiment #8 (Table 10) provided a favorable yet non-limiting embodiment of an inhalable formulation; the composition comprised MPs having an average volume diameter, $d_v$=2.53 μm±0.08. As shown in FIG. 2, 95% of the microparticles in this batch had particles sizes in an alveolar-respirable size range (1 μm to 3.5 μm). In non-limiting embodiments, Panel (b) of FIG. 1 shows the morphology of MPs produced from the spray dried NCs (i.e., NC-MPs). In certain non-limiting embodiments, the NC-MPs of the present disclosure may be produced using a nanocrystal-mannitol suspension comprising a feed concentration in a range of from about 0.45% to about 0.75% nanocrystals, a mannitol ratio in a range of from about 30% to about 50%, and a spray drying temperature in a range of from about 100° C. to about 120° C.

In certain non-limiting embodiments, the NC-MPs of the compositions have a sufficiently small average size (diameter $d_v$) distribution (e.g., 95% of particles) that they can enter alveoli, which have openings with an average size of approximately 3 μm or less. In certain non-limiting embodiments, the NC-MPs are sized to be able to enter bronchioles, i.e., have sizes at least in the range of from about 3 μm to about 5 μm, or less. In certain non-limiting embodiments, the NC-MPs are sized to be able to enter the trachea, i.e., have sizes at least in the range of from about 5 μm to about 10 μm, or less. The term "$d_g$" refers to geometric diameter. The term "$d_v$" refers to volume diameter. The term "$d_a$" refers to aerodynamic diameter. In certain non-limiting embodiments, the $d_v/d_g$ ratio of the NC-MP compositions of the present disclosure is in a range of from about 1.0 to about 1.5. In certain non-limiting embodiments, the $d_v/d_g$ ratio of the NC-MP compositions of the present disclosure is in a range of from about 1 to about 3.

In Vitro Aerosol Performance of SHetA2 NC-MPs

Figure 7:
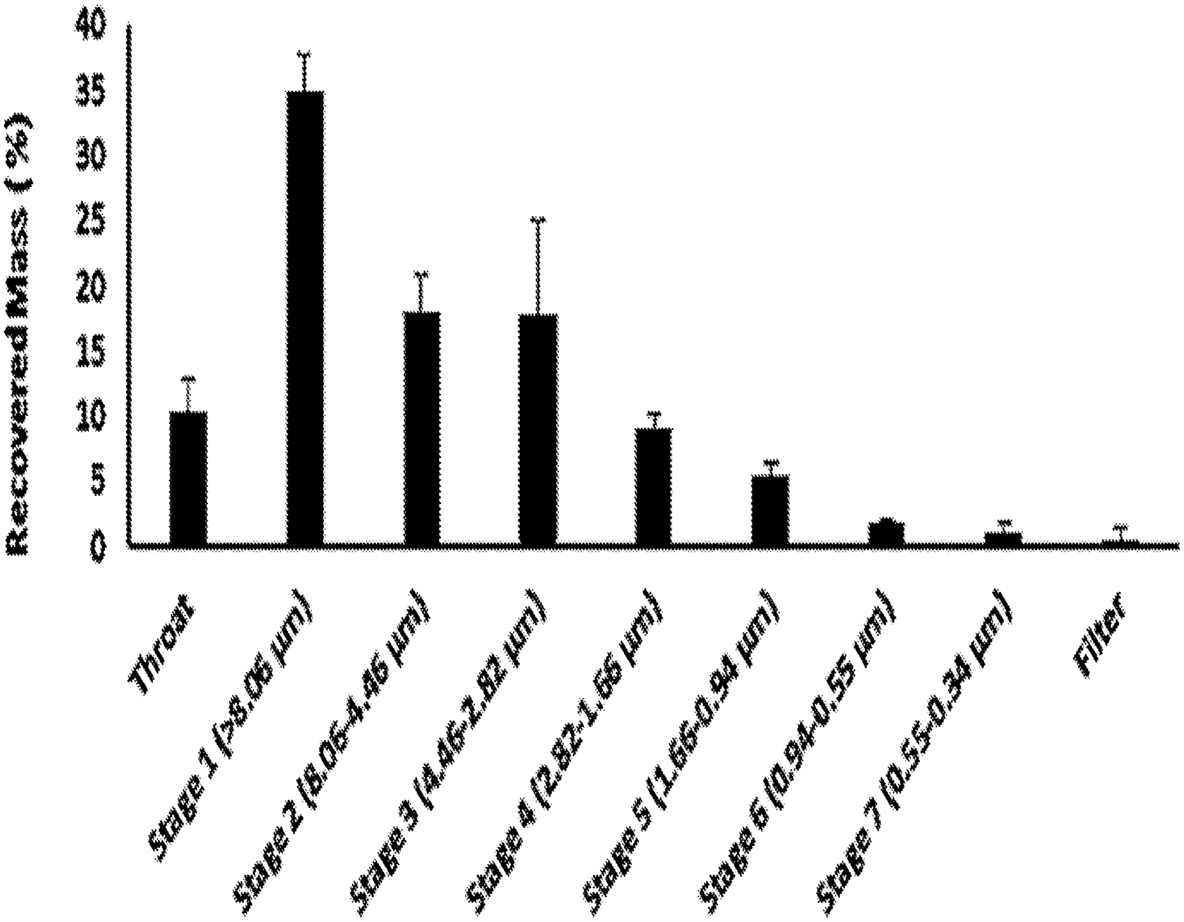
FIG. 7 shows in vitro aerosol performance of SHetA2 NC-MPs. SHetA2 deposition pattern in the collection cups of the Next Generation Impactor (NGI; Copley Scientific, Nottingham, UK) after dispersion of SHetA2 NC-MPs using SPIRIVA® HANDIHALER® (tiotropium bromide inhalation powder; Boehringer Ingelheim Pharmaceuticals, Inc., Ridgefield, CT).

The Next Generation Impactor (NGI) was employed in order to quantify in vitro lung deposition of SHetA2 NC-MPs. The NGI consists of eight collection cups corresponding to seven size fractionation stages of each of the regions of the respiratory tract. The deposition pattern of SHetA2 on the stages of NGI after aerosolization of SHetA2 NC-MPs powder using SPIRIVA® HANDIHALER® (tiotropium bromide inhalation powder; Boehringer Ingelheim Pharmaceuticals, Inc., Ridgefield, CT) is shown in FIG. 7. The amount of the emitted (delivered dose) drug recovered from the induction port (which mimics the human throat) was around 10.4%. Approximately 35% of the SHetA2 NC-MPs were larger than 8.06 μm, 18% were between 8.06 and 4.46 μm, and 18% were between 4.46 and 2.82 μm. The mass median aerodynamic diameter (MMAD) of the SHetA2 NC-MPs was found to be 3.24±0.15 μm with a GSD=1.6±0.2 (MMAD is defined as the diameter at which 50% of the particles by mass are larger and 50% are smaller). The emitted dose (ED) % and fine particle fraction ($FPF_{4.46}$) (%) were determined as 67.89±1.02 and 36.77±2.57, respectively. The FPF is the fraction of particles emitted by the device that would be deposited in the alveolar region of the lung (0.34-4.46 μm).

Apparent Maximum Solubility of SHetA2 NCs and SHetA2 NC-MPs

Figure 8:
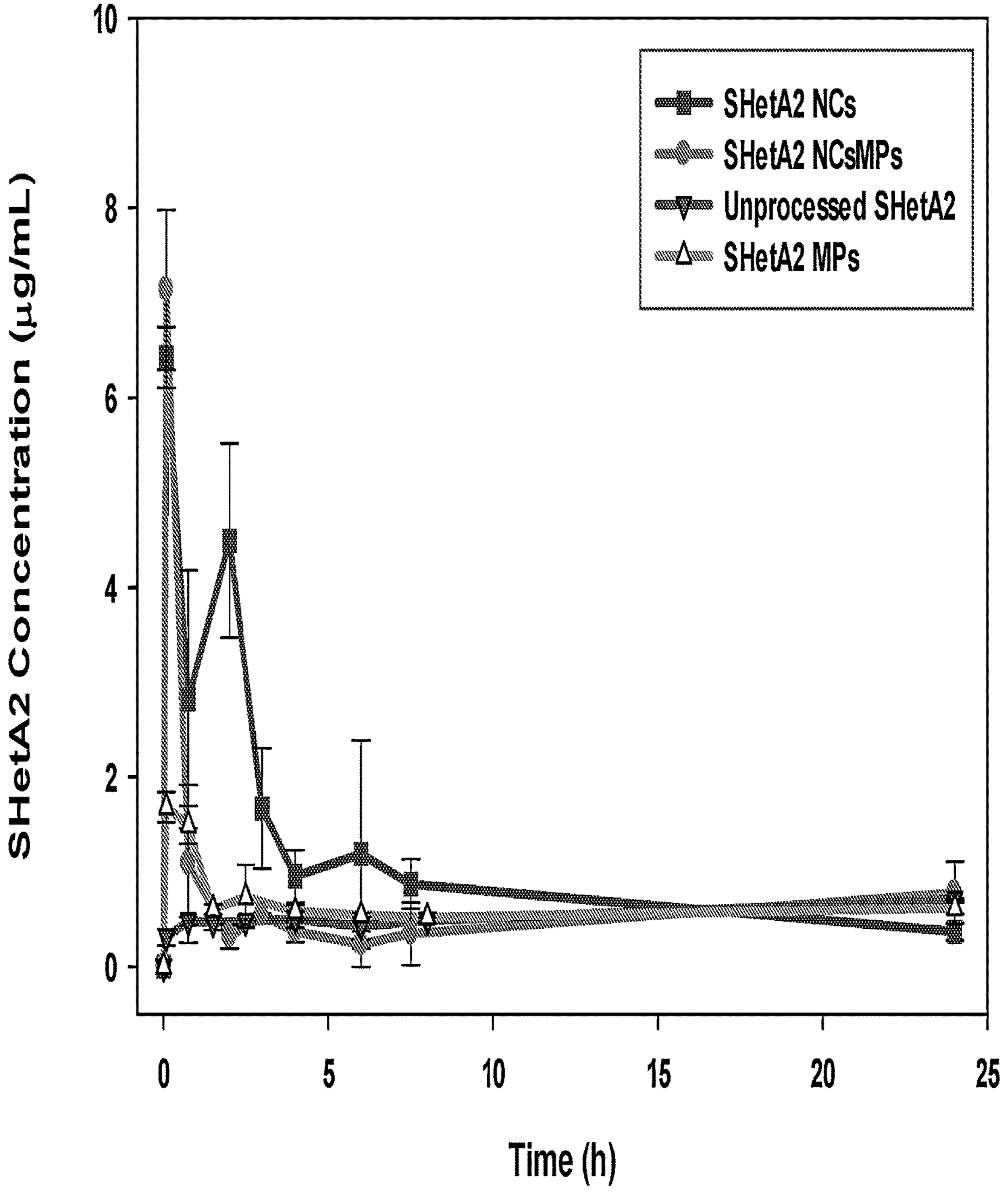
FIG. 8 shows apparent maximum solubilities of SHetA2 NCs and/or MPs from unprocessed SHetA2. SHetA2 NCs, SHetA2 MPs, and SHetA2 NC-MPs in PBS containing 0.05% SDS.

The apparent maximum solubility profiles of SHetA2 NCs, SHetA2 NC-MPs, unprocessed SHetA2 (i.e., unprocessed drug), and spray dried SHetA2 MPs (i.e., microparticulate amorphous drug) are shown in FIG. 8. The highest drug solubility was achieved at first 5 min by SHetA2 NC-MPs (7.14±0.84 μg/mL) followed by SHetA2 NCs (6.42±0.32 μg/mL), spray dried SHetA2 MPs (1.68±0.16 μg/mL), and unprocessed SHetA2 (0.48±0.11 μg/mL). Even though the spray dried SHetA2 MPs had amorphous structure, SHetA2 NC-MPs and SHetA2 NCs showed 4.24- and 3.82-fold higher apparent solubility, respectively (FIG. 8). SHetA2 NC-MPs and spray dried SHetA2 MPs followed a similar dissolution profile after 45 min. On the contrary, SHetA2 NCs showed a higher dissolution profile with a fluctuated pattern for the first 6 h due to growth of the NCs into bigger particles. At 45 min, the concentration of SHetA2 was 2.82±1.36 μg/mL; at 2 h, the SHetA2 concentration was 4.49±1.02 μg/mL; and in the 3-6 h period, the SHetA2 concentration decreased from 1.67 μg/mL to 1.19 μg/mL, respectively. After 6 h, SHetA2 NCs followed a similar dissolution profile with the other two formulations.

Figure 9:
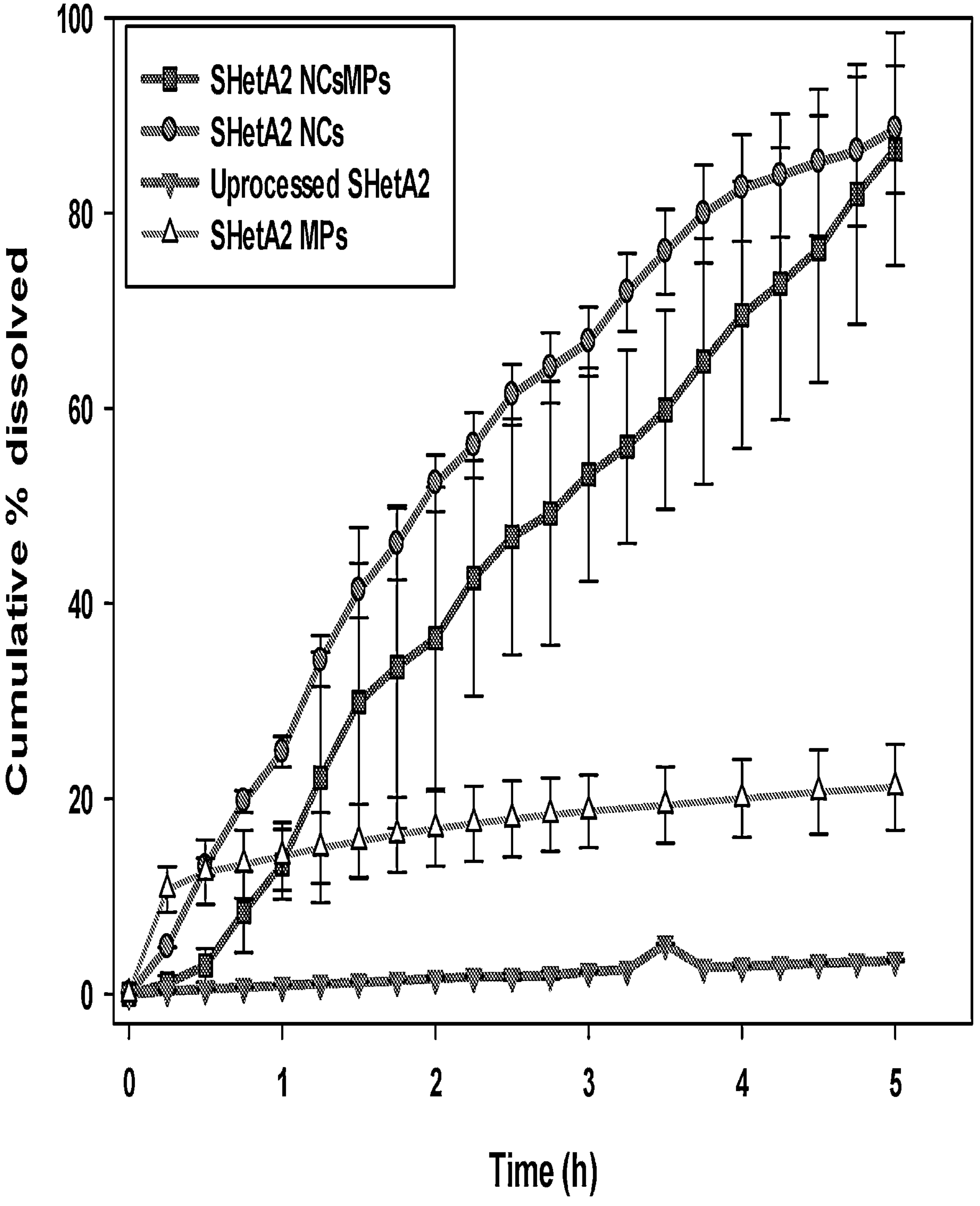
FIG. 9 shows dissolution profiles of SHetA2 NC-MPs, unprocessed SHetA2, and spray dried SHetA2 MPs of size range 2.82-4.46 μm. Cumulative percentage dissolved SHetA2 from unprocessed SHetA2, SHetA2 NCs, SHetA2 MPs, and SHetA2 NC-MPs.

Dissolution Profile of SHetA2 NC-MPs, Unprocessed SHetA2, and Spray Dried SHetA2 MPs of Size Range 2.82-4.46 μm The mean cumulative percentage of SHetA2 dissolved versus time data for SHetA2 NCs, SHetA2 NC-MPs, spray dried SHetA2 MPs, and unprocessed SHetA2 is shown in FIG. 9. MPs in sizes 2.82-4.46 μm were studied, because the particles in this size range are deposited in the alveolar region of the lungs. The cumulative percentage of SHetA2 dissolved for SHetA2 NCs and SHetA2 NC-MPs are significantly high compared to spray dried SHetA2 MPs and unprocessed SHetA2. The concentration of SHetA2 increased at a constant rate for SHetA2 NCs and SHetA2 NC-MPs until 5 h. The cumulative percentage of SHetA2 dissolved from SHetA2 NCs and SHetA2 NC-MPs reached 86.55±8.9% and 88.56±6.52%, respectively. In the case of spray dried SHetA2 MPs, there was a prompt release within the first 15 min, then SHetA2 concentration increased slowly until leveling at a cumulative percentage of 21.19±4.40%. In contrast, the unprocessed SHetA2 dissolved only 3.51±0.9%.

In Vivo Experiments

In vivo experiments were carried out to characterize the disposition (absorption, distribution, and elimination) of SHetA2 after pulmonary administration of SHetA2 NC-MPs and to make a comparison to that after pulmonary administration of SHetA2 MPs produced by spray-drying and oral administration of SHetA2 NCs.

MPs formed with SHetA2 NCs (NC-MPs) were administered to mice by the pulmonary routes (12.5 mg/kg and 25 mg/kg) and by oral routes and compared to the administration of 10 mg/kg of a SHetA2 suspension solution (4 mg/mL unprocessed SHetA2 in 0.2% of kolliphor). SHetA2 concentrations were determined in bronchio-alveolar lavage (BAL) and lung tissue at different time points.

Figure 3:
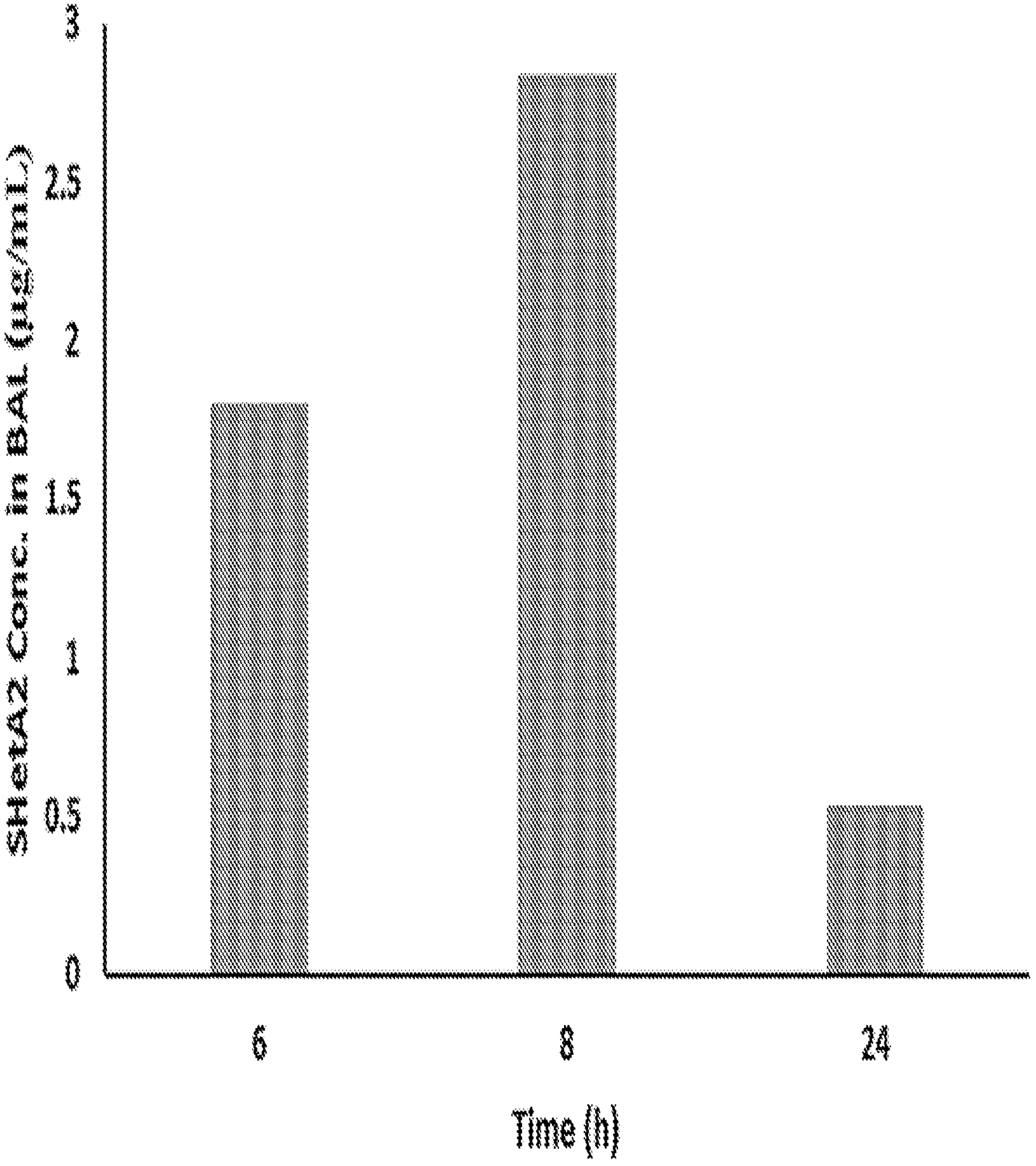
FIG. 3 shows concentration of SHetA2 in guinea pig BAL samples after administration of a 10 mg/kg dose of a SHetA2 suspension solution.

SHetA2 was detected in the BAL of animals dosed with 10 mg/kg of the SHetA2 suspension solution at 6, 8, and 24 hours post-administration, indicating that there was drug remaining to be absorbed from the airways into the lung tissue of these animals (FIG. 3). In contrast, no SHetA2 could be detected in the BAL of animals dosed with the NC-MPs at any time point, indicating that SHetA2 nanocrystals delivered as NC-MPs were dissolved and absorbed immediately upon delivery.

Figure 4:
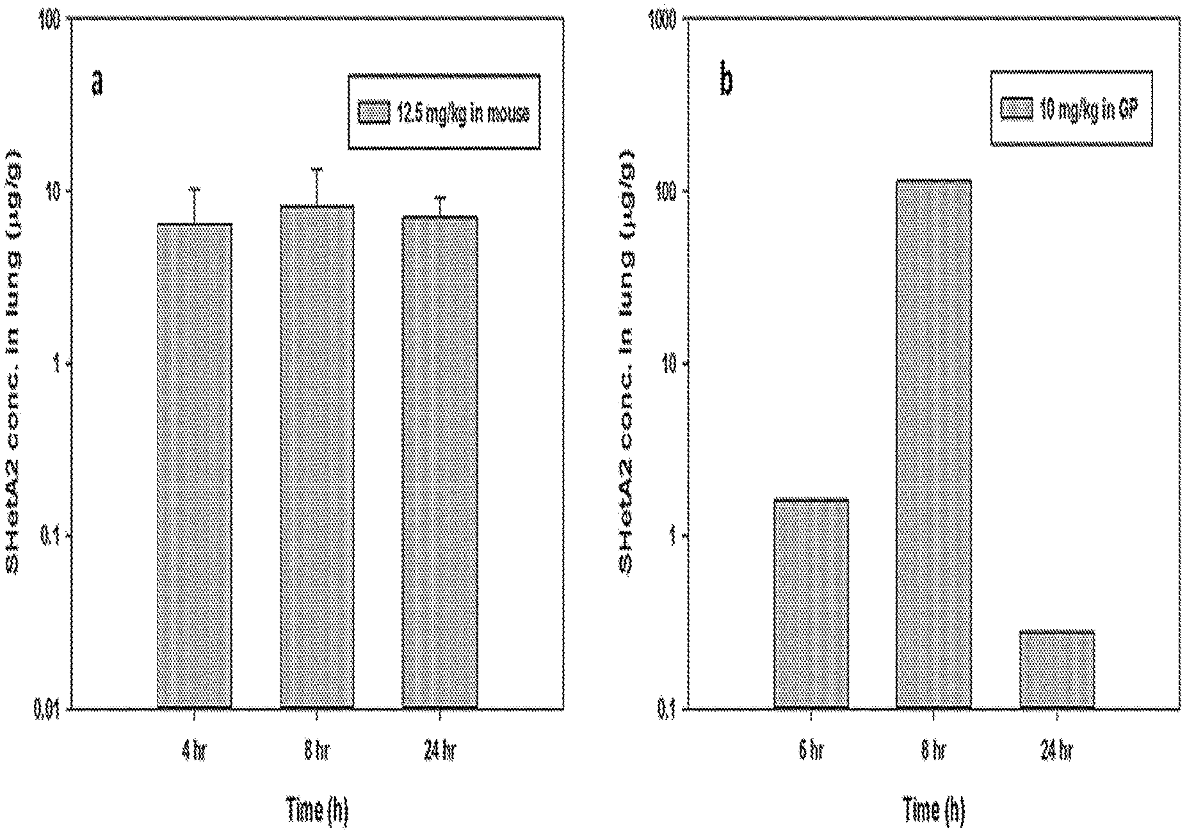
FIG. 4 shows a time-course distribution of SHetA2 concentrations in lung tissue after administration of (a) SHetA2 as NC-MPs and (b) a SHetA2 suspension solution.

Moreover, as shown in FIG. 4, while the SHetA2 concentrations in lung tissue were sustained and constant in lung tissue after pulmonary administration of SHetA2 NC-MPs (Panel (a) of FIG. 4), SHetA2 concentrations were variable after pulmonary administration of the SHetA2 suspension solution (Panel (b) of FIG. 4). This has important implications for the treatment of lung diseases, since SHetA2 delivery via NC-MPs results in lung concentrations which remain above therapeutic levels for the treatment of TB and cancer, while they are below therapeutic levels for TB treatment for a significant time period when SHetA2 is administered as the suspension solution. These results demonstrate that NC-MPs are more rapidly dissolved and absorbed into the lung tissue compared to SHetA2 administered as the suspension solution.

Figure 5:
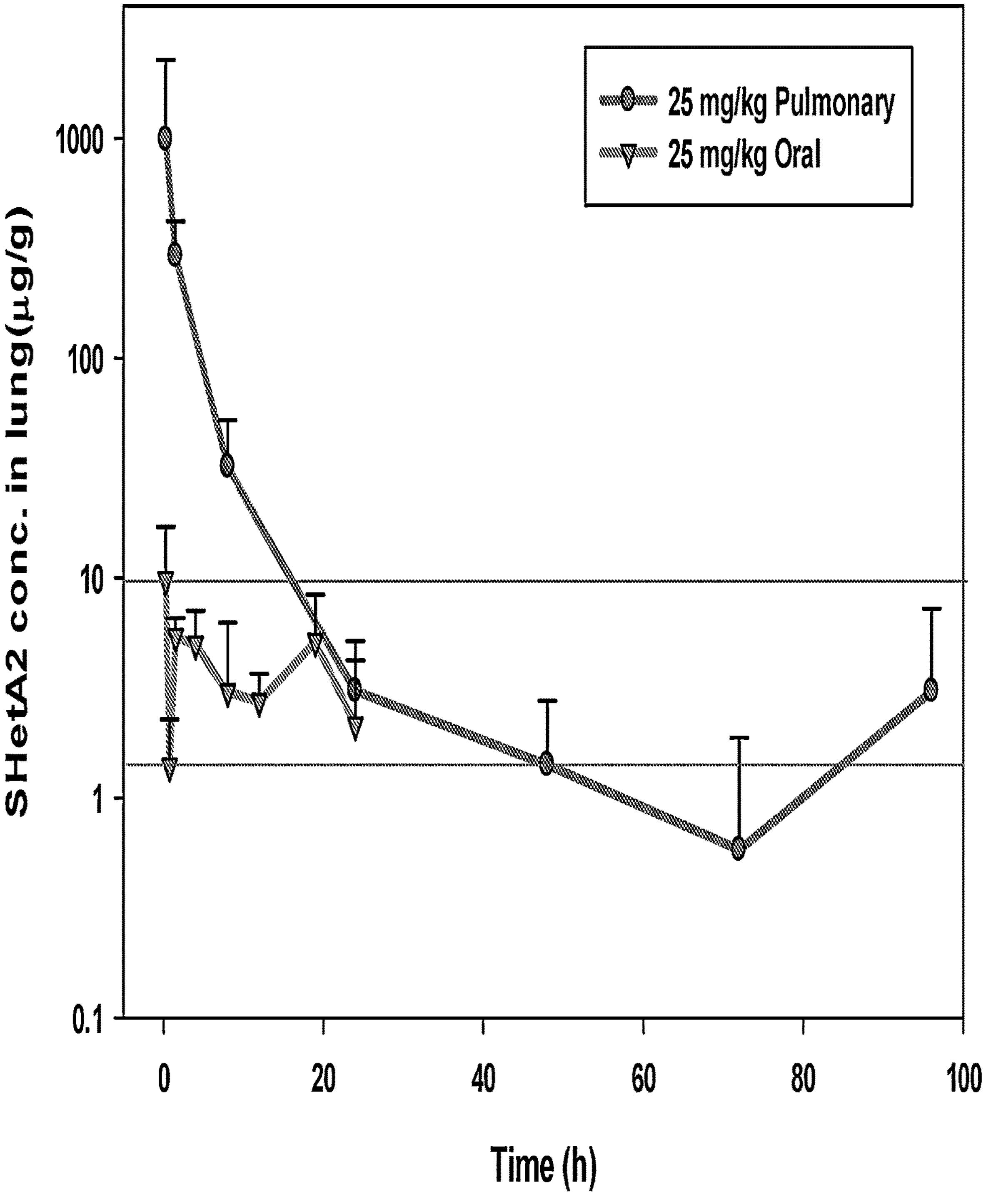
FIG. 5 shows SHetA2 concentrations in lung tissue after administration of NC-MPs via pulmonary and oral routes.

The comparison between lung tissue concentrations of SHetA2 NC-MPs after oral administration vs. pulmonary administration was studied, and the results are shown in FIG. 5. Lower concentrations of SHetA2 were observed at all times in the oral group compared to that after the pulmonary group (insufflation group). Moreover, drug concentrations were sustained after pulmonary administration and were detectable for a 4-fold longer duration compared to those after oral administration, demonstrating the superiority of delivering the NC-MP formulation via the pulmonary route. Pharmacokinetic parameters of the NC-MPs delivered via pulmonary vs. oral routes, including the area under the curve (AUC), apparent total body clearance (CL), elimination rate constant (K), half-life ($t_{1/2}$), and relative bioavailability were obtained by analyzing lung drug concentration measurements using PHOENIX® WINNONLIN® software (Certara, L. P., Princeton, NJ). Results are shown in Table 12.

The AUC after pulmonary administration was significantly larger than that after oral administration. The drug was cleared significantly faster from the lungs after oral administration compared to pulmonary administration, which is also evidenced by the 10-fold longer half-life when the drug is administered by the pulmonary route. Therefore, the apparent bioavailability of the drug is 30-fold larger after pulmonary administration using the oral route as reference. This demonstrates that pulmonary (versus oral) administration of NC-MPs significantly increased the bioavailability of SHetA2, and thus would also increase the bioavailability of other poorly soluble compounds.

Figure 6:
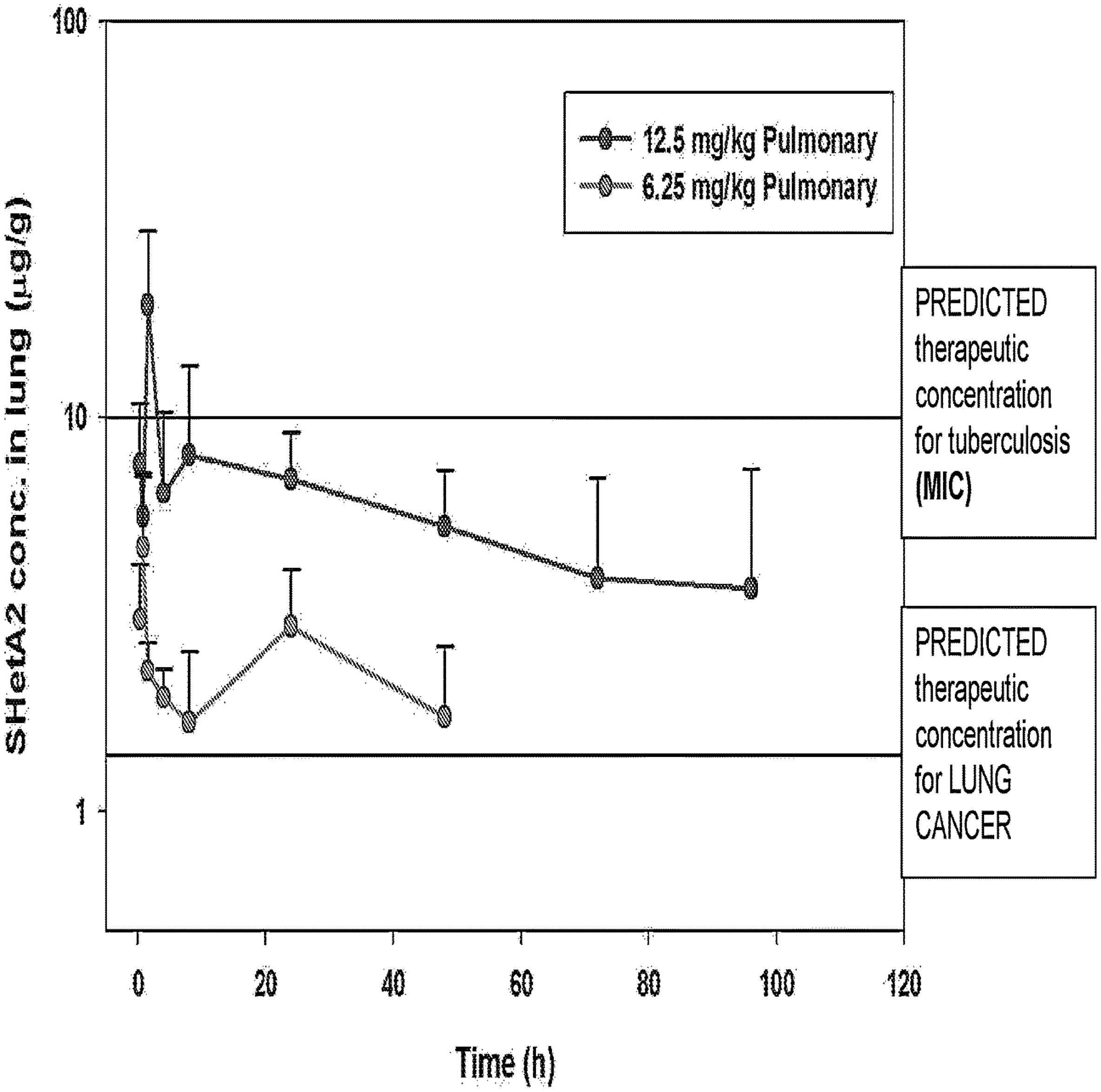
FIG. 6 shows SHetA2 lung concentration profiles in lungs over time for 12.5 mg/kg and 6.25 mg/kg doses after pulmonary administration.

Results from an experiment comparing drug concentration over time versus dosage (25 mg/kg and 12.5 mg/kg) with pulmonary administration of SHetA2 NC-MPs are shown in FIG. 6. Similar SHetA2 lung concentration profiles were observed between the two different doses, though the absolute concentration was greater for the higher dosage.

Pharmacokinetic parameters, including the AUC, apparent total body clearance (CL), elimination rate constant (K), half-life (t½), and relative bioavailability, were analyzed by PHOENIX® WINNONLIN® software (Certara, L. P., Princeton, NJ). As expected, pulmonary administration exhibited significantly larger AUC compared to the oral route. Also, there is a significant difference between CL of oral and pulmonary routes as a result of deposition of SHetA2 in the lungs. Regarding the half-lives of the two different routes, the difference is significantly large, again due to disposition of SHetA2 in the lungs.

In a particular embodiment, the present disclosure is directed to a method of producing a pharmaceutical composition comprising a dry powder formulation of a microparticulate drug composition, wherein the method comprises the steps of (i) producing by controlled precipitation a batch of nanocrystals consisting of a poorly soluble drug, wherein the controlled precipitation of the nancrystals is performed by (1) providing the poorly soluble dissolved drug in an organic solvent at a drug concentration in a range of from about 30 mg/ml to about 75 mg/ml, (2) combining the dissolved poorly soluble drug with an aqueous solvent to form a mixture, (3) sonicating the mixture at a sonication power density in a range of 0.5-5.0 Watts/Liter, a frequency of 10-100 Hz, and an amplitude of 10-80% for a time in a range of from about 20 minutes to about 90 minutes, and (4) ultrasonicating the mixture for a time in a range of from about 10 minutes to about 60 minutes, wherein the nanocrystals thereby formed have an average geometric diameter of less than about 0.2 μm, and wherein a micronization method is not used in the production of the nanocrystals, (ii) dispersing the batch of nanocrystals into a carrier solution, forming a nanocrystal/carrier suspension comprising a feed concentration in a range of from about 0.10% to about 2% nanocrystals, and a carrier ratio in a range of from about 10% to about 75%, (iii) spray drying the nanocrystal/carrier suspension at a spray drying temperature in a range of from about 80° C. to about 130° C. to form a microparticulate drug composition, wherein the microparticulate drug composition comprises microparticles comprising the nanocrystals dispersed in the carrier, wherein the microparticles have an average geometric diameter in a range of 1 μm to 500 μm, and wherein the microparticles have a dissolution rate that is at least about 5-fold higher than that of an unprocessed form of the poorly soluble drug and at least about 2-fold higher than that of microparticles comprising an amorphous form of the poorly soluble drug, that consist of the poorly soluble drug. The dry powder formulation may be a dry powder aerosol formulation. The average geometric diameter may be in a range of 1 μm to 400 μm. The aqueous solvent may be water.

In the method, the frequency may be in a range of, for example, about 50 to about 60 Hz. The feed concentration may be in a range of, for example, about 0.45% to about 0.75% nanocrystals. The carrier ratio may be in a range of, for example, about 30% to about 50%. The mixture may be sonicated for a time in a range of, for example, about 30 minutes to about 60 minutes. The mixture may be ultrasonicated for a time in a range of, for example, about 20 minutes to about 40 minutes. The spray drying temperature may be in a range of, for example, about 100° C. to about 120° C. The microparticles may comprise a ratio of the average volume diameter to the average geometric diameter in a range of, for example, about 1 to about 3. The carrier may be, for example, a highly-soluble sugar. The poorly soluble

TABLE 12

Pharmacokinetic parameters of the NC-MPs delivered via pulmonary vs. oral routes

| Treatment Route (dose) | AUC∞ (μg h/mL) | AUC dose (μg h/mL) | CL (L/h kg) | V (L/kg) | λ ($h^{-1}$) | $t_{1/2}$ (h) | MRT (h) | Cmax (μg/mL) | Tmax (h) |
|---|---|---|---|---|---|---|---|---|---|
| Oral 25 mg/kg | 6.17 | 3.80 | 101.24 | 1123.19 | 0.09 | 7.69 | 12.07 | 0.76 | 0.25 |
| Insufflation 12.5 mg/kg | 92.90 | 55.44 | 6.73 | 752.43 | 0.01 | 77.52 | 104.06 | 7.15 | 0.25 |

drug may be, for example, a heteroarotinoid. The heteroarotinoid may be selected from, for example, SHetA2, SHetA3, SHetA4, SHetC2, SHetD3, SHetD4, SHetD5, SHet50, SHet65, SHet100, OHet72, NHet17, NHet86, and NHet90. The poorly soluble drug may be, for example, a cyclin-dependent kinase 4 and 6 (CDK4/6) inhibitor. The CDK4/6 inhibitor may be selected from, for example, Palbociclib, Abemaciclib, Ribociclib, and ON123300. The poorly soluble drug may be a poly-ADP-ribose polymerase (PARP) inhibitor. The PARP inhibitor may be selected from, for example, Olaparib, Niraparib, Rucaparib, Talazoparib, Veliparib, Pamiparib, BMN673, CEP 9722, and E7016. The poorly soluble drug may be, for example, an Azabicyclooctan-3-one derivative. The Azabicyclooctan-3-one derivative may be selected from, for example, PRIMA-1 and PRIMA-$1^{MET}$. The poorly soluble drug may be, for example, a riminophenazine analog. The riminophenazine analog may be, for example, TBI-161, TBI-166, TBI-416, TBI-443, TBI-444, TBI-449, TBI-450, TBI-678, TBI-688, TBI-1002, TBI-1004, TBI-1010, and/or clofazimine.

While the present disclosure has been described herein in connection with certain non-limiting embodiments so that aspects thereof may be more fully understood and appreciated, it is not intended that the present disclosure be limited to these particular embodiments. On the contrary, it is intended that all alternatives, modifications, and equivalents are included within the scope of the present disclosure as defined herein. Thus the examples described above, which include particular embodiments including methods, will serve to show the practice of the present disclosure, the particulars shown are by way of example and for purposes of illustrative discussion of particular embodiments only and are presented in the cause of providing what is believed to be the most useful and readily understood description of procedures as well as of the principles and conceptual aspects of the present disclosure. Therefore, changes may be made in the formulation of the various compositions described herein, the methods described herein, or in the steps or the sequence of steps of the methods described herein without departing from the spirit and scope of the present disclosure as defined in the appended claims.

What is claimed is:

1. A method of producing a pharmaceutical composition comprising a dry powder formulation of a microparticulate drug composition, the method comprising the steps of:

producing by controlled precipitation a batch of nanocrystals consisting of a poorly soluble drug, wherein the controlled precipitation of the nanocrystals is performed by:

(1) providing the poorly soluble drug dissolved in an organic solvent at a drug concentration in a range of from about 30 mg/ml to about 75 mg/ml, wherein the organic solvent is miscible in an aqueous solvent, (2) combining the poorly soluble drug dissolved in the organic solvent with an aqueous solvent to form a mixture, (3) sonicating the mixture at a sonication power density in a range of 0.5-5.0 Watts/Liter, a frequency of 10-100 Hz, and an amplitude of 10-80% for a time in a range of from about 20 minutes to about 90 minutes, and (4) ultrasonicating the mixture for a time in a range of from about 10 minutes to about 60 minutes, wherein the poorly soluble drug is a heteroarotinoid or cyclin-dependent kinase 4 and 6 (CDK4/6) inhibitor, wherein the nanocrystals thereby formed have an average geometric diameter of less than about 0.2 μm, and wherein a micronization method is not used in the production of the nanocrystals;

dispersing the batch of nanocrystals into a carrier solution consisting of a carrier and an aqueous solvent, thereby forming a nanocrystal/carrier suspension having a feed concentration in a range of from about 0.10% to about 2% nanocrystals, and a carrier ratio in a range of from about 10% to about 75%; and spray drying the nanocrystal/carrier suspension at a spray drying temperature in a range of from about 80° C. to about 130° C. to form a microparticulate drug composition, wherein the microparticulate drug composition comprises microparticles consisting of the nanocrystals dispersed in the carrier, wherein the microparticles have an average geometric diameter in a range of about 1 μm to about 500 μm, and wherein the microparticles have a dissolution rate that is at least about 5-fold higher than that of an unprocessed form of the poorly soluble drug and at least about 2-fold higher than that of microparticles comprising an amorphous form of the poorly soluble drug, that consist of the poorly soluble drug.

2. The method of claim 1, wherein at least one of:

the frequency is in a range of about 50 Hz to about 60 Hz;

the feed concentration is in a range of about 0.45% to about 0.75% nanocrystals;

the carrier ratio is in a range of about 30% to about 50%; and/or the spray drying temperature is in a range of about 100° C. to about 120° C.

3. The method of claim 1, wherein at least one of:

the mixture is sonicated for a time in a range of about 30 minutes to about 60 minutes; and/or the mixture is ultrasonicated for a time in a range of about 20 minutes to about 40 minutes.

4. The method of claim 1, wherein the microparticles comprise a ratio of the average volume diameter to the average geometric diameter in a range of about 1 to about 3.

5. The method of claim 1, wherein the carrier is a highly-soluble sugar.

6. The method of claim 1, wherein the heteroarotinoid is selected from SHetA2, SHetA3, SHetA4, SHetC2, SHetD3, SHetD4, SHetD5, SHet50, SHet65, SHet100, OHet72, NHet17, NHet86, and NHet90.

7. The method of claim 1, wherein the CDK4/6 inhibitor is selected from Palbociclib, Abemaciclib, Ribociclib, and ON123300.

8. The method of claim 1, wherein the aqueous solvent is water.

9. The method of claim 1, wherein the pharmaceutical composition is formulated for administration as a dry powder aerosol.

10. The method of claim 1, wherein the microparticles have an average geometric diameter in a range of about 1 μm to 40 about μm.

11. The method of claim 9, wherein the method further comprises disposing the pharmaceutical composition in an inhaler for pulmonary delivery of the pharmaceutical composition.

12. The method of claim 11, wherein the microparticles have an average geometric size that enables the pharmaceutical composition to target and be deposited in an alveolar region of at least one lung.

13. The method of claim 1, wherein the microparticles have an average geometric diameter in a range of about 50 μm to 500 about μm.

14. The method of claim 1, wherein the pharmaceutical composition is in the form of a capsule or tablet.

15. The method of claim 14, wherein at least one of:

the pharmaceutical composition is packaged in a gelatin capsule;

the pharmaceutical composition is combined with a methyl cellulose to produce the tablet; and/or the method further comprises the use of at least one compression process to produce the tablet.

16. A method of producing a pharmaceutical composition comprising a dry powder formulation of a microparticulate drug composition, the method comprising the steps of:

producing by controlled precipitation a batch of nanocrystals consisting of a poorly soluble drug, wherein the controlled precipitation of the nanocrystals is performed by:

(1) providing the poorly soluble drug dissolved in an organic solvent at a drug concentration in a range of from about 30 mg/ml to about 75 mg/ml, wherein the organic solvent is miscible in an aqueous solvent, (2) combining the poorly soluble drug dissolved in the organic solvent with an aqueous solvent to form a mixture, (3) sonicating the mixture at a sonication power density in a range of 0.5-5.0 Watts/Liter, a frequency of 10-100 Hz, and an amplitude of 10-80% for a time in a range of from about 20 minutes to about 90 minutes, and (4) ultrasonicating the mixture for a time in a range of from about 10 minutes to about 60 minutes, wherein the poorly soluble drug is a heteroarotinoid or cyclin-dependent kinase 4 and 6 (CDK4/6) inhibitor, wherein the nanocrystals thereby formed have an average geometric diameter of less than about 0.2 μm, and wherein a micronization method is not used in the production of the nanocrystals;

dispersing the batch of nanocrystals into a carrier solution consisting of a carrier and an aqueous solvent, thereby forming a nanocrystal/carrier suspension having a feed concentration in a range of from about 0.10% to about 2% nanocrystals, and a carrier ratio in a range of from about 10% to about 75%; and spray drying the nanocrystal/carrier suspension at a spray drying temperature in a range of from about 80° C. to about 130° C. to form a microparticulate drug composition, wherein the microparticulate drug composition comprises microparticles consisting of the nanocrystals dispersed in the carrier, wherein the microparticles have an average geometric diameter in a range of about 1 μm to about 500 μm, and wherein the microparticles have a dissolution rate that is at least about 5-fold higher than that of an unprocessed form of the poorly soluble drug and at least about 2-fold higher than that of microparticles comprising an amorphous form of the poorly soluble drug, that consist of the poorly soluble drug; and wherein the pharmaceutical composition is in the form of a capsule or tablet.

17. The method of claim 16, wherein the microparticles have an average geometric diameter in a range of about 50 μm to 500 about μm.

* * * * *